United States Patent
Chediak et al.

(10) Patent No.: US 7,221,455 B2
(45) Date of Patent: May 22, 2007

(54) INTEGRATED, FLUORESCENCE-DETECTING MICROANALYTICAL SYSTEM

(75) Inventors: J. Alex Chediak, Eagan, MN (US); Zhongsheng Luo, Albany, CA (US); Timothy D. Sands, West Lafayette, IN (US); Nathan W. Cheung, Albany, CA (US); Luke P. Lee, Orinda, CA (US); Jeonggi Seo, Albany, CA (US)

(73) Assignee: The Regents of the Unversity of California, Oakland, CA (US)

( * ) Notice: Subject to any disclaimer, the term of this patent is extended or adjusted under 35 U.S.C. 154(b) by 253 days.

(21) Appl. No.: 10/903,477

(22) Filed: Jul. 30, 2004

(65) Prior Publication Data

US 2005/0157301 A1    Jul. 21, 2005

Related U.S. Application Data

(60) Provisional application No. 60/537,540, filed on Jan. 20, 2004.

(51) Int. Cl.
*G01N 21/25* (2006.01)
*G01N 21/26* (2006.01)
*G01N 21/64* (2006.01)
*G01J 1/58* (2006.01)

(52) U.S. Cl. .................. 356/419; 356/417; 422/82.08; 250/458.1; 250/459.1; 436/172

(58) Field of Classification Search ............. 356/417, 356/419; 422/82.05, 82.07, 82.08, 82.09, 422/82.11

See application file for complete search history.

(56) References Cited

U.S. PATENT DOCUMENTS 5,517,313 A * 5/1996 Colvin, Jr. ................. 356/417
5,650,123 A * 7/1997 Saini et al. ............. 422/82.11

(Continued)

OTHER PUBLICATIONS

J.A. Chediak, "Evaluation of (In,Ga)N Films as Optical Absorption Filters For Application in Integrated Fluorescence Detection Micro-Bioanalytical Systems", Masters Thesis, Engineering-Materials Science and Engineering, Graduate Division, Unversity of California, Berkeley, Fall 2001, pp. 1-48.

(Continued)

*Primary Examiner*—Roy M. Punnoose
(74) *Attorney, Agent, or Firm*—Michaelson & Associates; Peter L. Michaelson; George Wolken, Jr.

(57) ABSTRACT

The present invention relates to a functionally integrated microanalytical system for performing fluorescence spectroscopy. A source of fluorescence-exciting radiation, typically a LED, is integrated onto a substrate along with a photodetector and, in some embodiments, an optical filter. A pixel-to-point laser lift-off process is used to effect this component integration. For those cases in which a filter is required, a thin film bandgap filter is typically used, such as CdS or $CdS_xSe_{1-x}$ ($0<x<1$). A disposable microchannel containing the sample and its fluorescent tag is mounted onto the integrated assembly of LED, photodetector and (optionally) filter. This configuration of components allows the microchannel and sample to be readily removed and replaced, facilitating rapid analysis of multiple samples. Multiple LEDS, detectors and filters (if present) can also be integrated onto the same substrate, permitting multiple wavelength analysis of the sample to be performed concurrently.

20 Claims, 17 Drawing Sheets

U.S. PATENT DOCUMENTS

| | | | | |
|---|---|---|---|---|
| 5,933,233 | A | * | 8/1999 | Gunther ..................... 356/318 |
| 6,071,795 | A | | 6/2000 | Cheung et al. ............. 438/458 |
| 6,241,948 | B1 | * | 6/2001 | Watkins et al. .......... 422/82.05 |
| 6,335,263 | B1 | | 1/2002 | Cheung et al. ............. 438/455 |
| 6,420,242 | B1 | | 7/2002 | Cheung et al. ............. 438/458 |
| 6,632,400 | B1 | | 10/2003 | Brennen et al. ......... 422/82.01 |
| 6,743,581 | B1 | * | 6/2004 | Vo-Dinh ........................ 435/6 |
| 6,940,590 | B2 | * | 9/2005 | Colvin et al. ............... 356/218 |
| 2003/0235924 | A1 | * | 12/2003 | Adams et al. .............. 436/172 |

OTHER PUBLICATIONS

J.A. Chediak et al., "Evaluation of (In,Ga)N Films as Optical Absorption Filters For Application in Integrated Fluorescence Detection Micro-Bioanalytical Systems", Proceedings of the Materials Research Society Symposium, vol. 693, pp. I11.13.1-I11.13.6 (2002).

P.M. Goodwin et al, "Single-Molecule Detection in Liquids by Laser-Induced Fluorescence", Acc. Chem. Res., 1996, vol. 29, pp. 607-613.

H.S. Kwok et al, "Growth of CdSxSe1-x Thin Films by Laser Evaporation Deposition", Appl. Phys. Lett., vol. 52, No. 21 May 23, 1988, pp. 1815-1816.

H.S. Kwok et al, "Growth of Highly Oriented CdS Thin Films by Laser-Evaporation Deposition", Appl. Phys. Lett., vol. 52, No. 13, Mar. 28, 1988, pp. 1095-1097.

Z.S. Luo et al, "Enhancement of (In,Ga)N Light-Emitting Diode Performance by Laser Liftoff and Transfer from Sapphire to Silicon", IEEE Photonics Technology Letters, vol. 14, No. 10, Oct. 2002, pp. 1400-1402.

J. Roulet et al, "Performance of an Integrated Microoptical System for Fluorescence Detection in Microfluidic Systems", Analytical Chemistry, vol. 74, No. 14, Jul. 15, 2002, pp. 3400-3407.

J.R. Webster et al, "Monolithic Capillary Electrophoresis Device with Integrated Fluorescence Detector", Analytical Chemistry, vol. 73, No. 7, Apr. 1, 2001, pp. 1622-1626.

Su-Huai Wei et al, "First-Principles Calculation of Band Offsets, Optical Bowings, and Defects in CdS, CdSe, CdTe, and Their Alloys", Journal of Applied Physics, vol. 87, No. 3, Feb. 1, 2000, pp. 1304-1311.

* cited by examiner

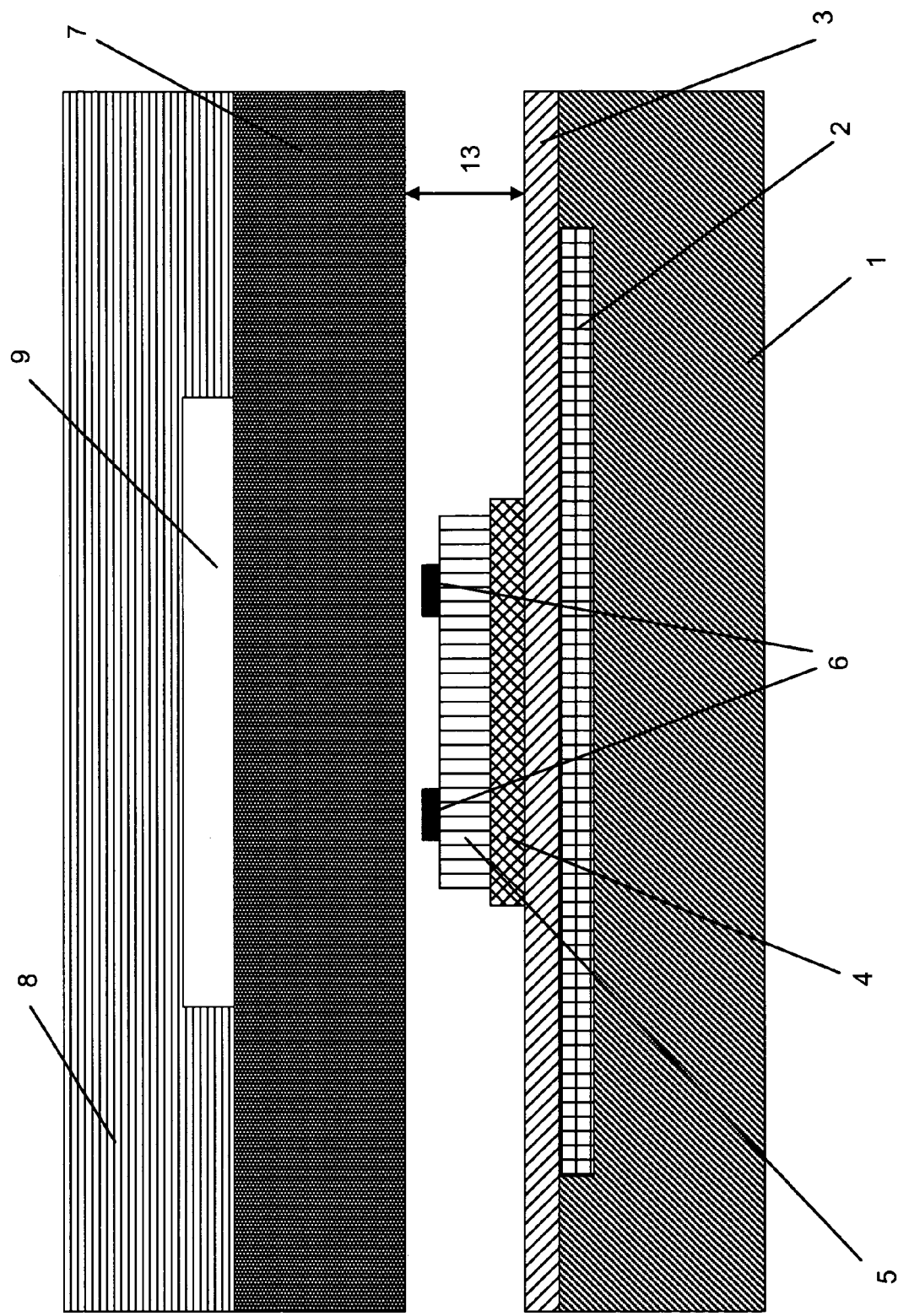

(a) Microfluidic channel fabrication

INTEGRATED, FLUORESCENCE-DETECTING MICROANALYTICAL SYSTEM

CROSS REFERENCE TO RELATED APPLICATIONS

Pursuant to one or more of 35 U.S.C. § 119, 120, 363 and 365, this application claims priority from provisional patent application Ser. No. 60/537,540 filed Jan. 20, 2004, the entire contents of which is incorporated herein by reference for all purposes.

STATEMENT REGARDING FEDERALLY SPONSORED RESEARCH OR DEVELOPMENT

This invention was made with Government support under NSF Grant (Contract) #DMI-0088145. The Government has certain rights to this invention.

BACKGROUND OF THE INVENTION

1. Field of Invention

This invention relates generally to the field of spectroscopic detection, identification and/or characterization of substances and, more particularly, to fluorescence detection, identification and/or characterization performed by an integrated microanalytical system, as well as to materials, fabrication techniques and methods of use of such a microanalytical system.

2. Description of the Prior Art

Optical spectroscopy is a common technique for the detection, identification and/or characterization of many substances including atoms, molecules, ions, polymers, thin films, biological substances, among others. We describe herein primarily the detection of molecules pursuant to various embodiments of the present invention, understanding thereby that the descriptions herein are not limited simply to detection of molecules but can include identification, characterization and the acquisition of other information concerning the material under study. For economy of language, we use "detection" to refer to all such process. Similarly, the descriptions herein are not limited to molecules but can include other forms of matter as apparent to those having ordinary skills in the art, collectively described herein as "molecules".

One important type of optical spectroscopy involves the excitation of a molecule to an excited electronic state, typically by absorption of radiation in the ultraviolet, visible or near-infrared regions of the spectrum. The electronically excited molecule then returns to its ground state, or to a lower-lying electronic state, accompanied by the emission of radiation. Detection and measurement of the properties of this emitted radiation provide important information concerning the molecule.

Many molecules of interest are not conveniently detected directly by fluorescence detection but advantageously employ a fluorescence-facilitating molecule selectively attached to the sample molecule whose detection and/or characterization is desired. That is, a molecule having favorable properties for fluorescence detection (typically a dye) is chosen or manufactured such that it selectively bonds to the sample whose detection is desired. The sample thus "tagged" is then subject to fluorescence detection. To be concrete in our descriptions, we focus chiefly on those examples in which tagging a sample with a dye molecule is an advantageous preliminary step in fluorescence detection. However, this is by way of illustration and not limitation since various embodiments of the present invention can be employed when several different tagging dyes are used, or in those cases in which the sample itself can be subject to fluorescence detection without the need for tagging. In addition, we use the term "dye" for economy of language to indicate any fluorescence-facilitating substance bonded to the sample, not restricted to other, possibly more restrictive, chemical definitions of dyes.

A distinction is sometimes made between "phosphorescence" and "fluorescence" with fluorescence indicating radiation emitted from the absorbing molecule essentially immediately following absorption and excitation; that is, emission follows absorption by less than about 1 millisecond. Phosphorescence may be used to denote a longer-delayed emission following absorption. However, such distinctions are not necessary in describing embodiments of the present invention. For economy of language, we use "fluorescence" to indicate emission of radiation following absorption, irrespective of the time delay between absorption and emission.

An important characteristic of fluorescence spectroscopy (or "fluorescence detection") is its high sensitivity, often achieving detection limits several orders of magnitude lower than detection limits achievable with other analytical techniques. Thus, fluorescence detection is a widely used laboratory bench technique for bioassay applications as well as other analyses. However, bench-top systems are typically expensive as well as bulky, unsuited for use in the field or at remote locations.

Physicians, biologists and others routinely use bench-top instrumentation typically costing in excess of $100,000 to inspect biological fluids, excite reactions in chemicals to generate structural information, or to detect toxins by tagging molecules with fluorescing agents. These bench-top instruments typically include an enclosed laser that contributes to the physical size and expense. Miniaturization of this equipment would be expected to lead to a drastic reduction in cost as well as portability. Furthermore, since a miniaturized system is likely to be highly integrated, its use by laypersons is expected to be feasible. Thus, a need exists in the art for miniaturized fluorescence detection analytical systems including systems with lower cost, improved portability as well as high functionality and reliability.

SUMMARY OF THE INVENTION

The present invention relates to functionally integrated microanalytical systems (or "microsystems") for performing fluorescence spectroscopy, including materials and methods for fabricating such microsystems. Important advantages of such microsystems include lower cost and improved portability, both tending to broaden the range of potential applications of fluorescence spectroscopy for bioassay and chemical applications, in the field as well as in the laboratory.

Various embodiments of the present invention include Si-based microsystems and corresponding fabrication processes that integrate excitation, filtering and photodetection. Similar functionality to bench-top fluorescence detection equipment is achieved in some embodiments of the present invention by replacing the gas laser typically used in bench-top systems with a thin-film Light-Emitting-Diode (LED). In addition, a thin-film filter, typically single layer, can be used in place of the grating, bulk glass, or distributed-Bragg-Reflector (DBR) commonly used in bench-top systems.

In comparison with bench-top systems, microsystems are typically less expensive and more compact, making them better suited for use in the field. In addition, some embodiments of the present invention combine many or all of the non-disposable components on a single substrate while hygienically and/or chemically isolating disposable components (typically microfluidic components). This component segregation typically enables the microsystem to evaluate many samples sequentially.

Some embodiments of the present invention include multicolored LEDs with matching filters, integrated into a single microsystem. Such embodiments permit multiple bioassays or chemical analyses of a single or multiple samples to be performed simultaneously.

In summary, advantages of the present invention include, but are not limited to: 1) A compact portable design suited for field applications. 2) Hygienic separation of disposable and non-disposable components for rapid sequential testing. 3) Integration of multicolored LEDs with matching filters for simultaneous bioassays and/or chemical detections. 4) Lower fabrication costs than typical bench-top systems.

The lower fabrication costs make the present microsystems an attractive alternative to conventional bench-top systems for in-lab use. In addition, the portability of the present microsystems make them particularly advantageous for field uses including but not limited to: 1) Field medical assessments of patients in civilian or military situations in which rapid analysis is critical. 2) Environmental detection of chemical and biological agents.

BRIEF DESCRIPTION OF THE DRAWINGS

The drawings herein are not to scale and the depictions of relative sizes and scale of components within a drawing are schematic and also not to scale.

To facilitate understanding, identical reference numerals have been used, where possible, to designate identical elements that are common to the figures.

The teachings of the present invention can readily be understood by considering the following detailed description in conjunction with the accompanying drawings in which:

FIG. 1 is a schematic cross-sectional depiction of an integrated microanalytical system with a single light source probing a single sample.

Figure 1A:
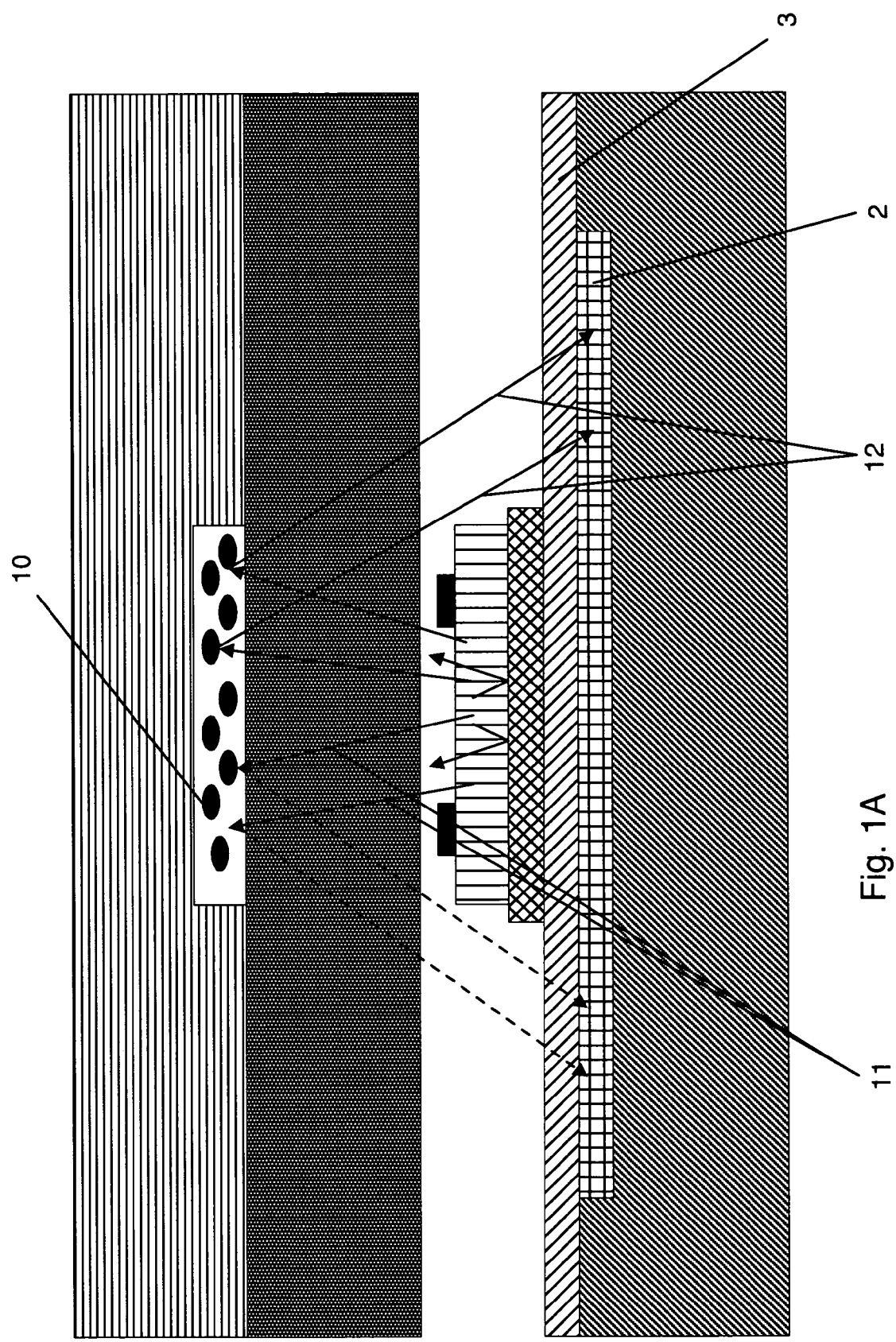

FIG. 1A is the schematic cross-sectional depiction of FIG. 1 including typical paths of excitation radiation from the light source to the sample, and of emitted radiation from the sample to the photodetector.

FIG. 2 depicts results of computer simulations for filter transmission as a function of both wavelength and incident angle for: (2A) A 2.4 μm CdS filter. (2B) A 90 layer ZnS/NaAlF DBR stack. (2C) Band shift as a function of incident angle for three different DBR stacks and a CdS filter. (2D) The cutoff wavelength (1% transmission) as a function of percent thickness variation for three different DBR stacks and a CdS filter.

Figure 3:
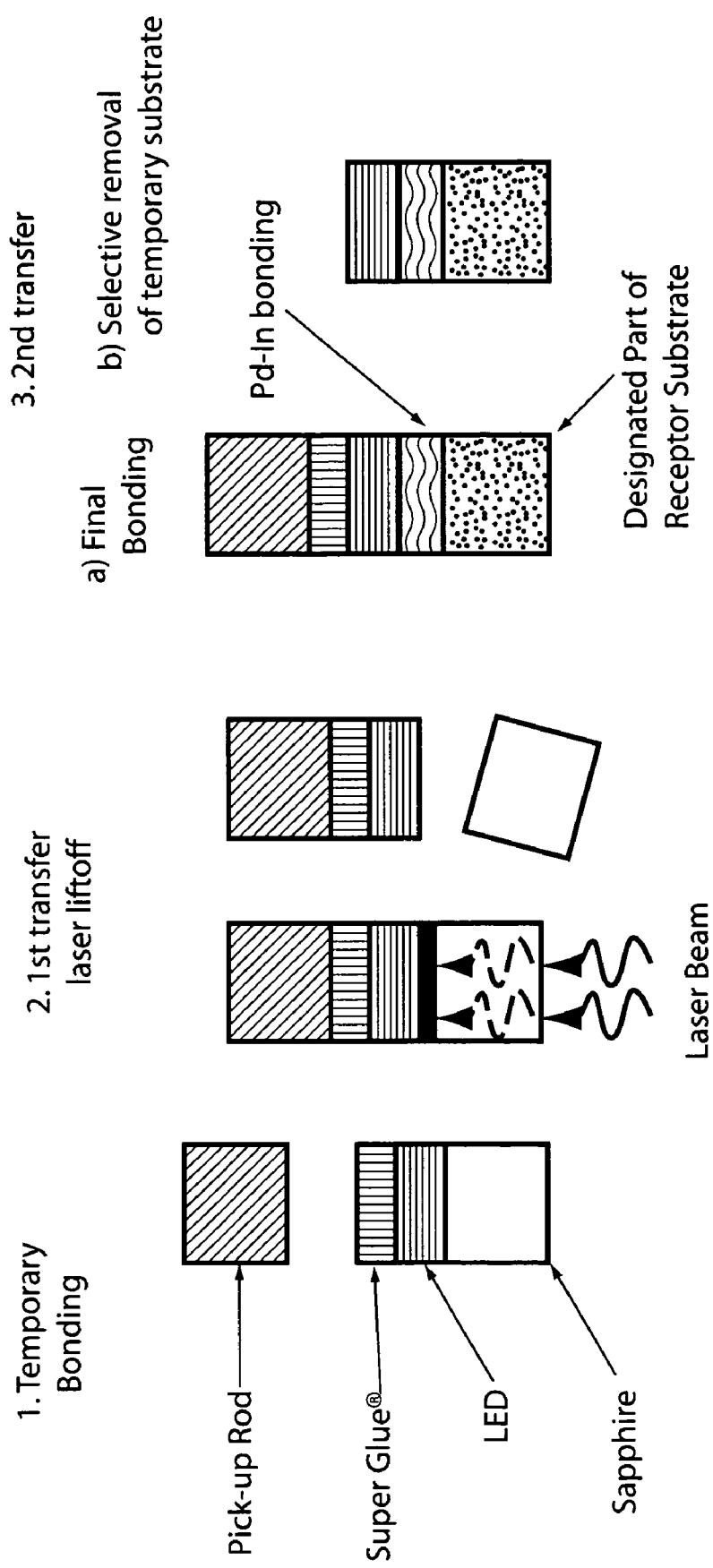

FIG. 3 is a schematic depiction of a typical pixel-to-point LED transfer process.

Figure 4:
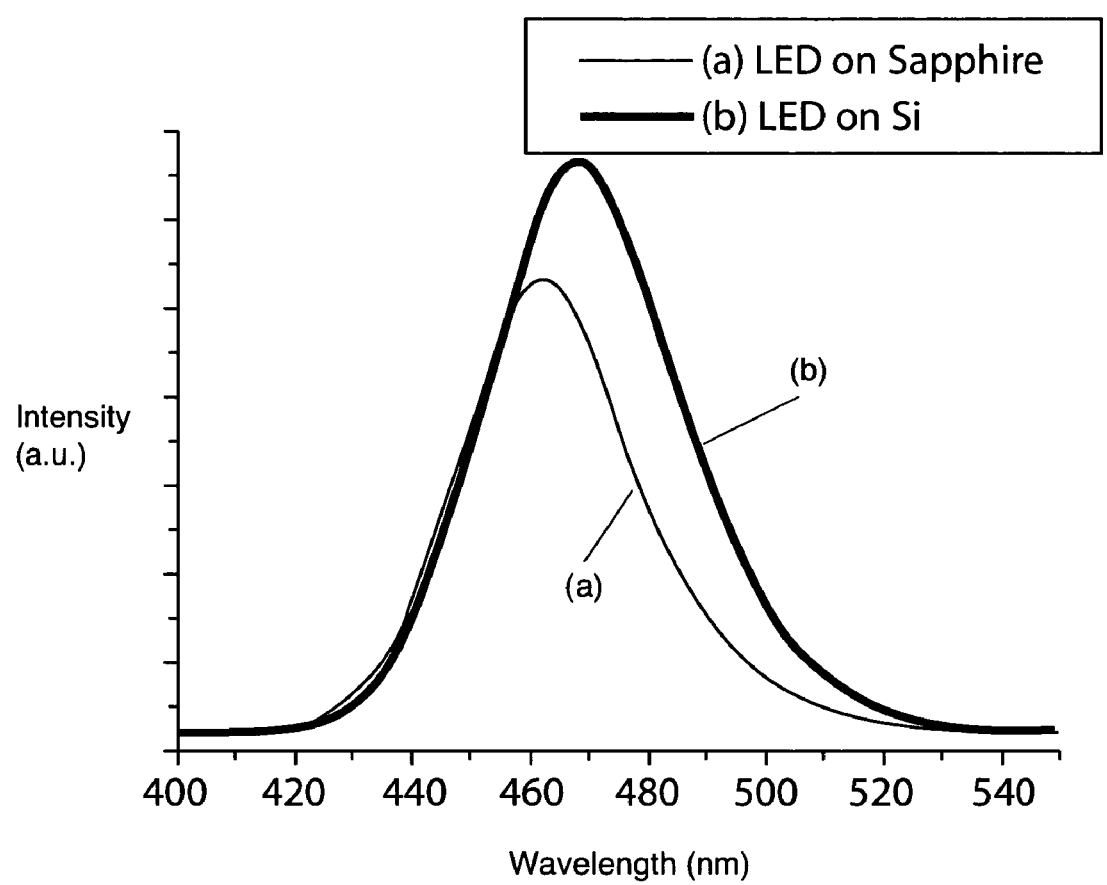

FIG. 4 is the emission spectra of a typical GaN LED on its sapphire growth substrate (a), and after laser lift-off and transfer to a silicon substrate (b).

Figure 5:
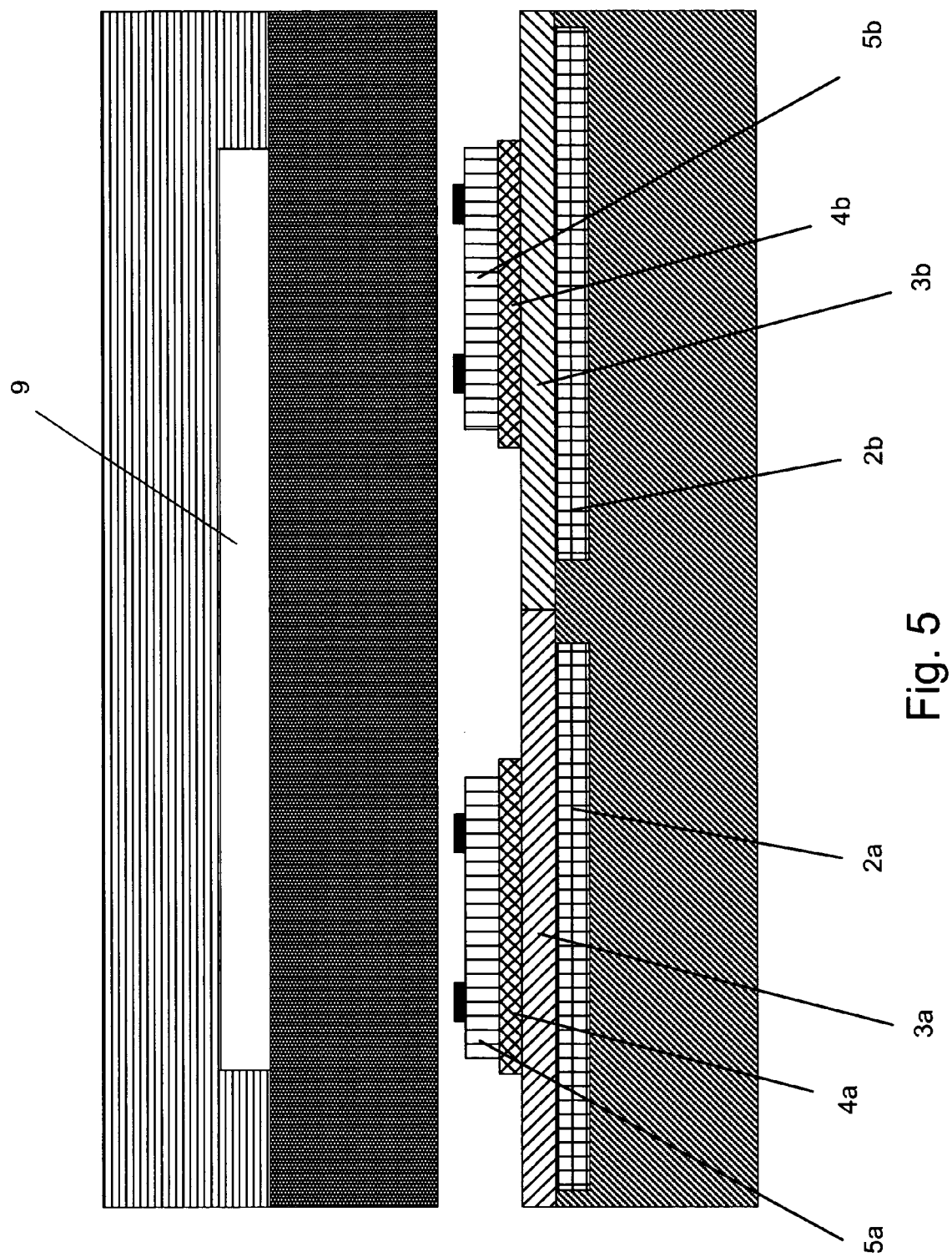

FIG. 5 is a schematic cross-sectional depiction of multiple light sources probing a single sample container.

Figure 6:
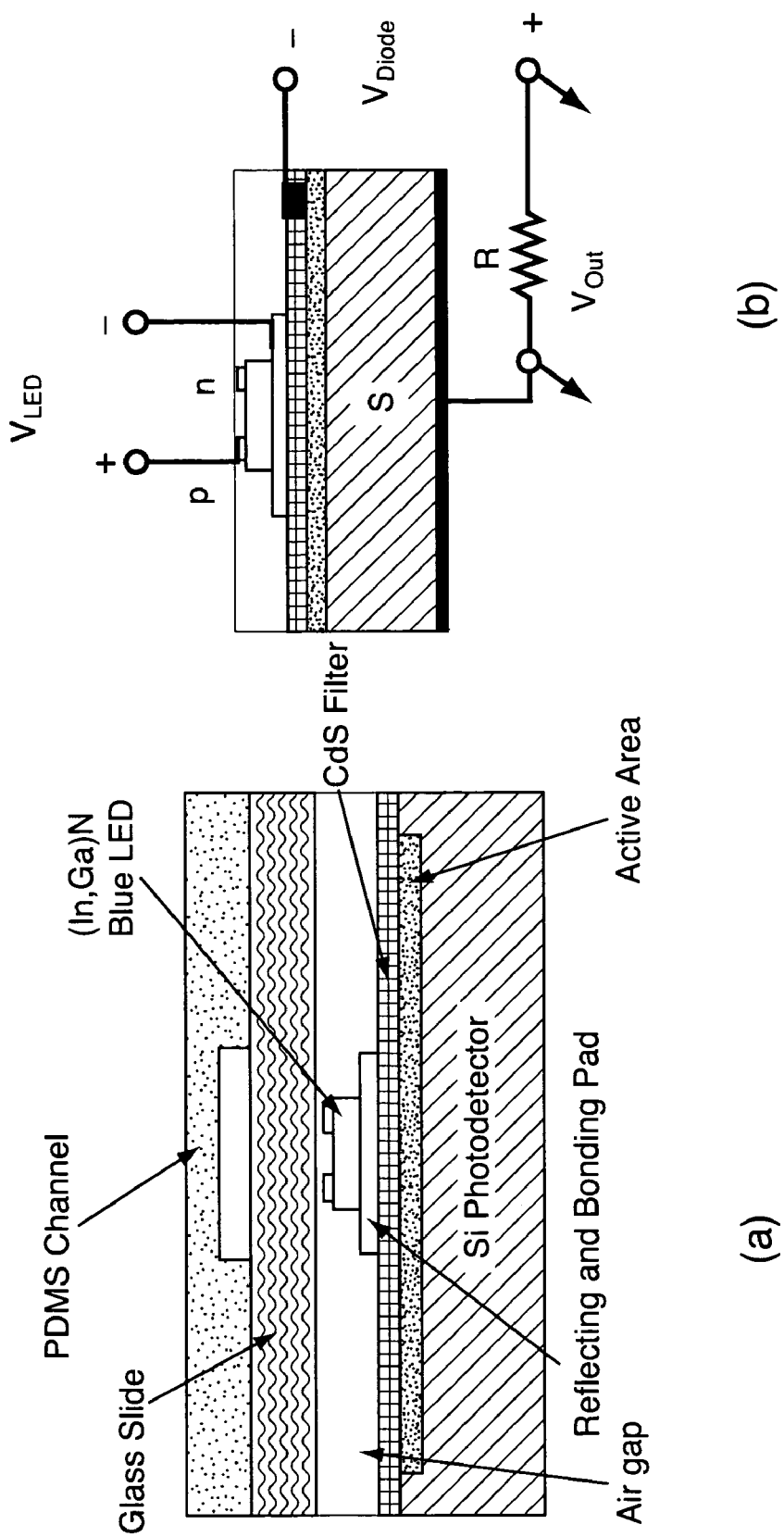

FIG. 6 is a schematic, cross-sectional depiction of the heterogeneous integration of a CdS filter with an (In, Ga)N LED, a Si PIN photodetector and a microfluidic device (a), and typical wiring (b).

Figure 7:
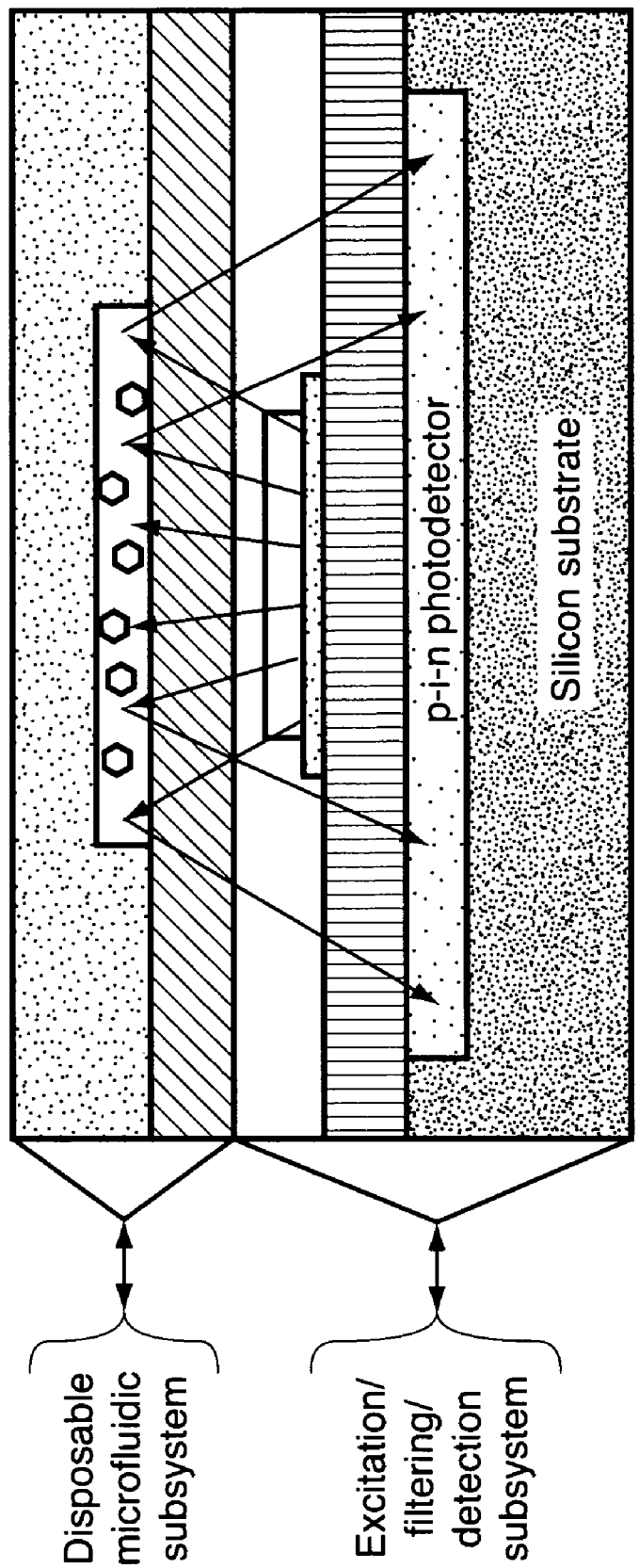

FIG. 7 is a schematic depiction as in FIG. 6(a) indicating sample molecules, and typical light paths for the excitation and Stokes' shifted emission signals.

Figure 8:
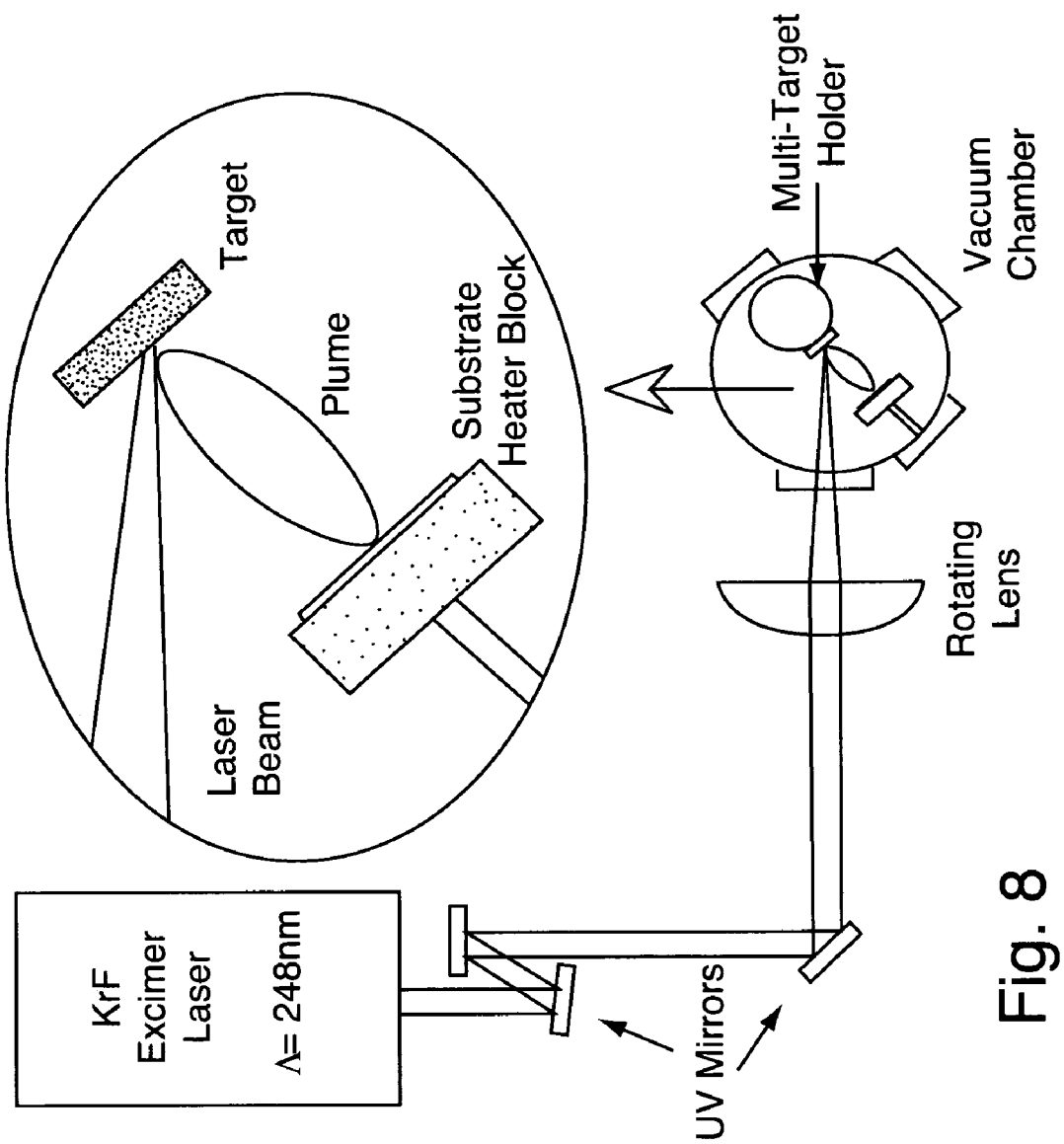

FIG. 8 is a schematic depiction of a typical KrF excimer laser pulsed laser deposition (PLD) system operating at 248 nm wavelength.

Figure 9:
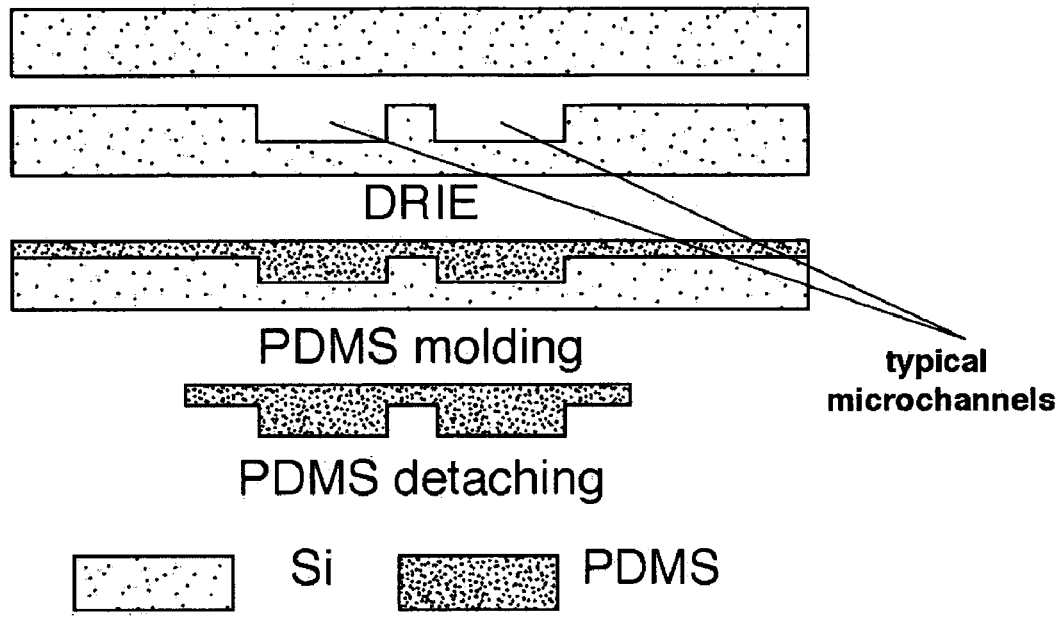
Figure 9:
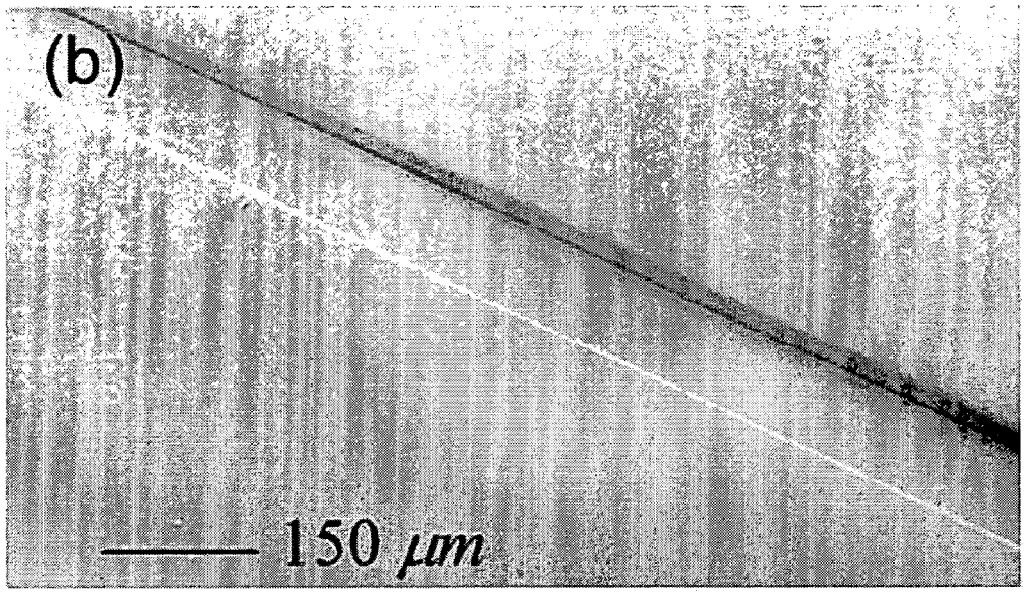

FIG. 9 is a schematic, cross-sectional depiction of a typical microfluidic fabrication process (a), and a scanning electron micrographic image of a fabricated microchannel (b).

Figure 10:
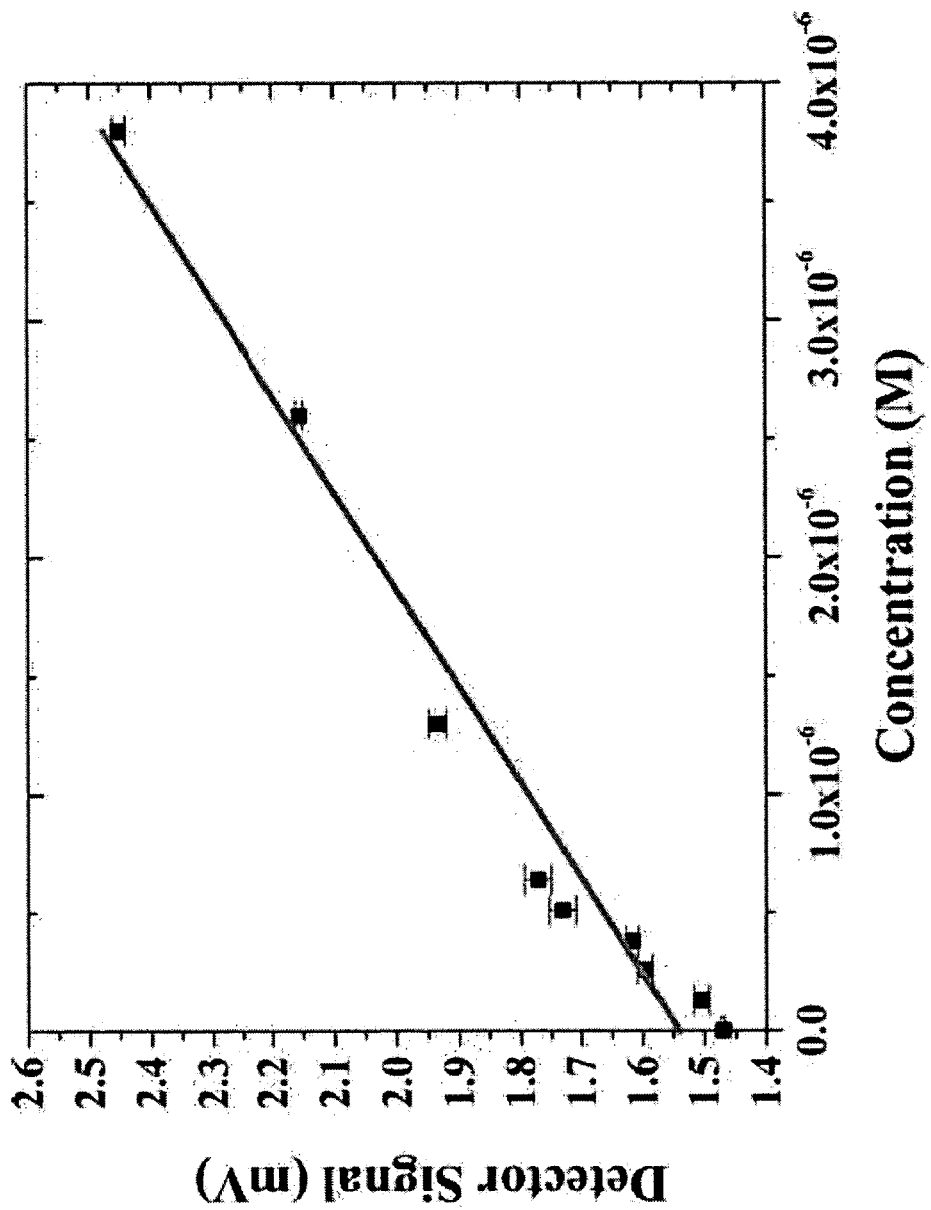

FIG. 10 shows the emission signal at the detector in millivolts (mV) as a function of molar sample concentration (M) produced by a typical microanalytical system pursuant to some embodiments of the present invention.

Figure 11:
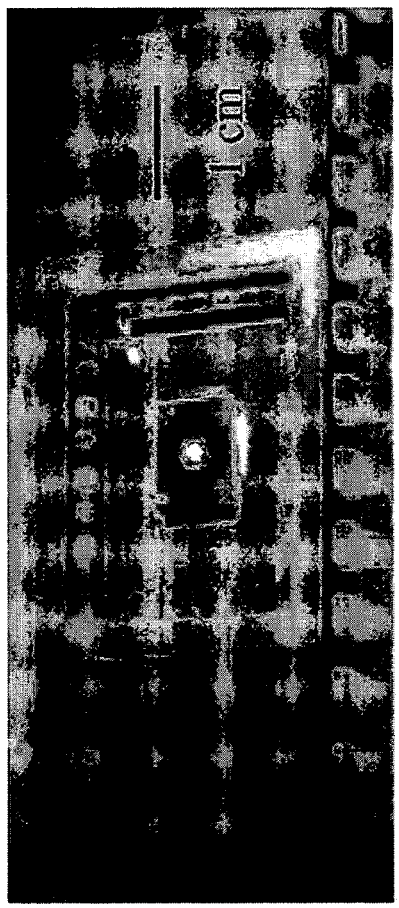
Figure 11:

FIG. 11 shows a prototype microsystem pursuant to some embodiments of the present invention with the LED power on (a), and exciting a sample in the microfluidic device (b).

Figure 12:
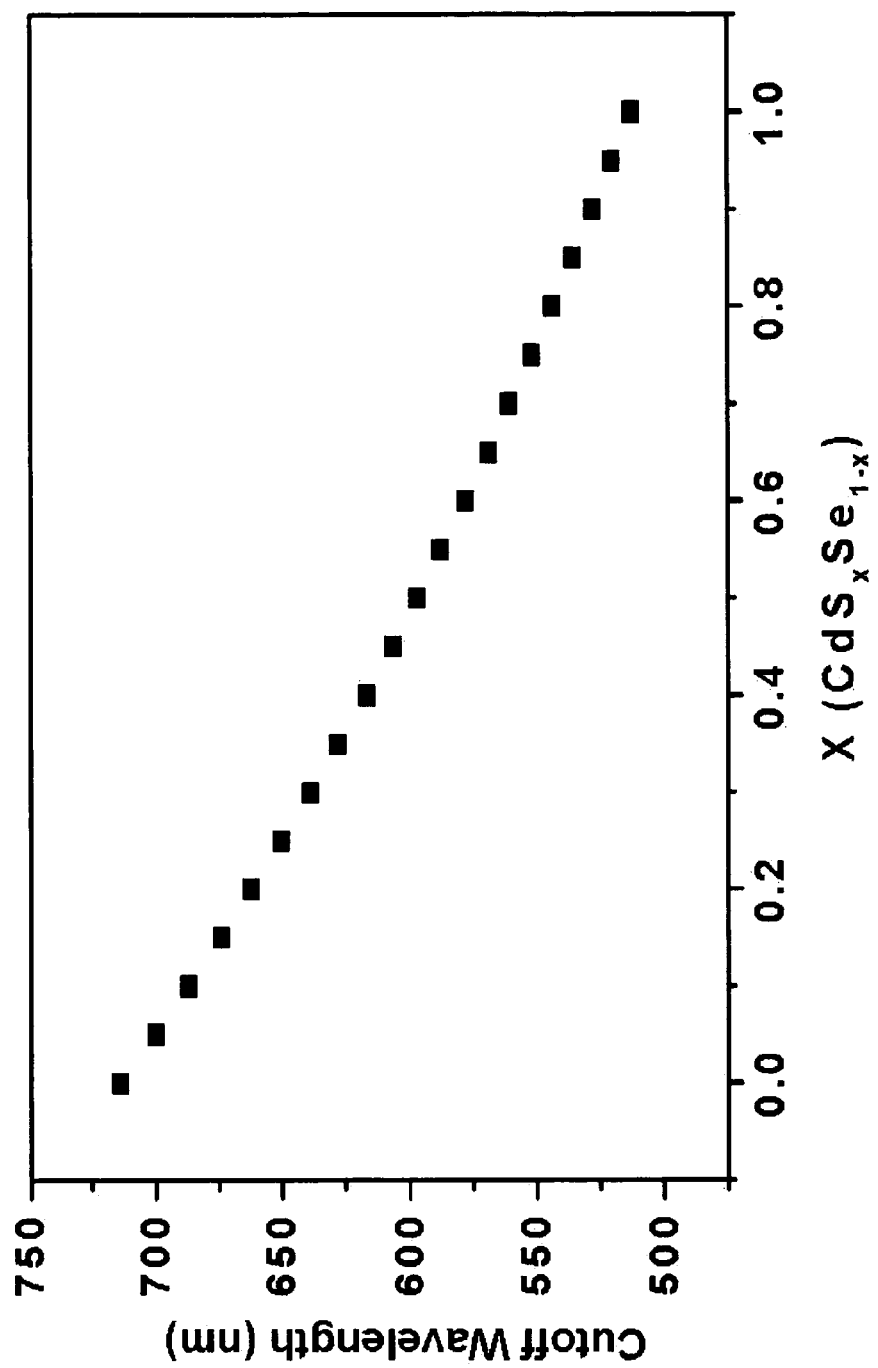

FIG. 12 depicts the cutoff wavelength (corresponding to the absorption edge) of an $CdS_xSe_{1-x}$ filter as a function of the filter's composition measured by the value of x (0<x<1).

Figure 13:
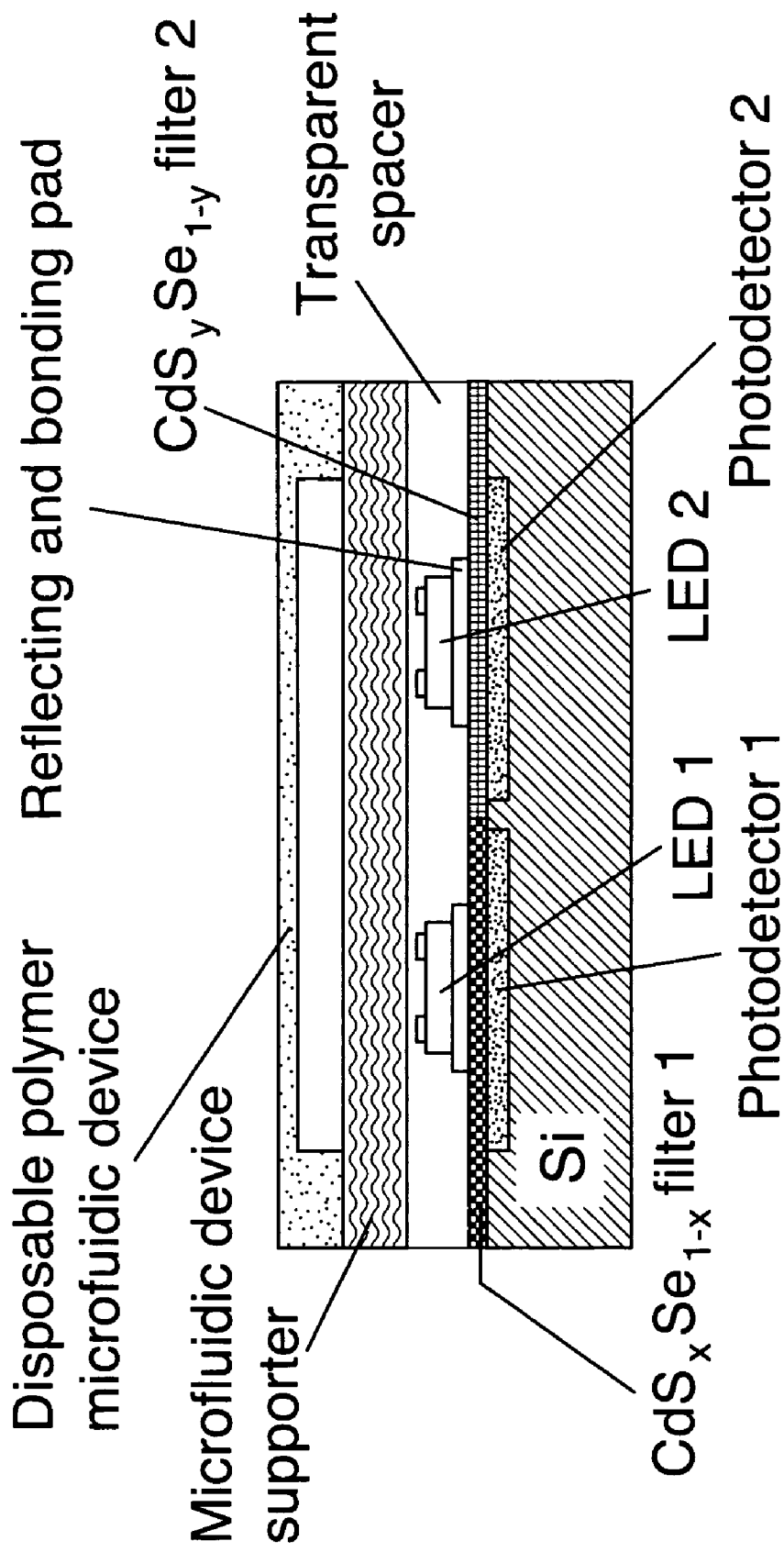

FIG. 13 is a schematic cross-sectional view of a typical two-color fluorescent detection microsystem pursuant to some embodiments of the present invention.

DETAILED DESCRIPTION OF THE INVENTION

The present invention relates to functionally integrated microanalytical systems (or "microsystems") for performing fluorescence spectroscopy, including materials and methods for fabricating such microsystems. Such integration and miniaturization draws upon advances in the integration and miniaturization of silicon-based microelectronics, but has several significant differences. For example, integrated microanalytical systems typically include one or more light sources, one or more filters to distinguish excitation and emitted radiation, one or more sample chambers and at least one light detection means (typically including amplification circuitry). Integrating these components into a unified package presents challenges distinct from those encountered in silicon-based microcircuit miniaturization.

In addition to material incorporated herein from provisional patent application Ser. No. 60/537,540 (including its references and attachments), some embodiments of the present invention relate to subject matter contained in Attachments A, B, C, and D, attached hereto, made a part hereof, and incorporated herein by reference for all purposes.

Attachment A: "Heterogeneous Integration of CdS Filters with GaN LEDs for Fluorescence Detection Microsystems." By: J. Alex Chediak, Zhongshen Luo, Jeonggi Seo, Nathan Chang, Luke P. Lee, Timothy D. Sands, *Sensors and Actuators A*, Vol. 111, pp. 1–7 (2004).

Attachment B: "Development of Selective Absorption Filters for Integrated Fluorescence Microsystems," a report submitted in partial satisfaction of the requirements for the degree of Doctor of Philosophy in Engineering—Materials Science and Engineering in the Graduate Division of the University of California, Berkeley by Juan Alexander Chediak, Spring 2004.

Attachment C: "Pixel-to-Point Transfer: A Process for Integrating Individual GaN-Based Light-Emitting Devices into Heterogeneous Microsystems," by Z. S. Luo, T. Sands, N. W. Chung, J. A. Chediak, J. Seo and L. P. Lee, *Mat. Res. Soc. Symp. Proc.*, Vol. 768, pp. G4.8.1–G4.8.5 (2003).

Attachment D: Revised version of presentation made at the 45*th Electronic Materials Conference*, Salt Lake City, Utah, Jun. 25–27, 2003 entitled "Heterogeneous integration of (In, Ga)N light-emitting Diodes, Cd (S, Se) filters and Silicon Photodetectors for Fluorescence-detecting microanalytical Systems" by Zhongshen Luo, J. Alex Chediak, Jeonggi Seo, Nathan Chang, Luke P. Lee, Timothy D. Sands.

FIG. 1 depicts in cross-sectional view (not to scale) the structure of a typical microsystem pursuant to some embodiments of the present invention. FIG. 1 depicts a single light source 5 and a single sample chamber 9. Other embodiments include multiple light sources with a single sample chamber, or multiple light sources with multiple sample chambers.

Bench-top systems for performing laser-induced fluorescence typically include gas lasers directing light onto a sample chamber containing the sample molecules to be detected and/or otherwise characterized. The sample molecules may optionally be bound to various (or various combinations) of dyes to facilitate fluorescence. Following absorption of the incident light, the molecules "fluoresce" and emit light at a different (longer) wavelength. The wavelength difference between the absorption and emission is called the Stokes' shift. Table I gives Stokes' shifts for various dyes commonly used in laser-induced fluorescence, given in nm=nanometers=$10^{-9}$ meters.

Neither excitation nor emission of radiation from a sample occur at infinitely precise wavelengths. For example, absorption of radiation by a sample occurs over a range of wavelength values about a local "peak" of absorption (that is, a local point of maximum absorbance). Typically, samples may have numerous local absorption peaks over a considerable wavelength range comprising an absorption spectrum for the sample. The width of the absorption band can be sharp or broad depending on numerous factors including the nature of the sample, the nature of the quantum transition responsible for the absorption, the temperature and physical environment of the absorbing species, among many other factors. Emission of radiation from the sample similarly occurs over a band. For economy of language, we will refer simply to a "wavelength" of absorption or emission, understanding thereby that the wavelength of the peak intensity of an absorption or emission band is intended. If the breadth and/or shape of an absorption or emission line is relevant to an understanding of the effect, special mention will be made.

The fluorescence-exciting light source 5 used in various embodiments of the microanalytical system is advantageously a light-emitting-diode (LED). However, this is not an essential limitation as other light sources can be employed, including vertical cavity surface emitting lasers, among other laser types and configurations. LEDs are relatively inexpensive sources of light but may have the disadvantage of emitting radiation in or near the wavelength band of the fluorescence emissions. When such spectral overlap is a concern, it is advantageous to employ a combination of appropriate light source and filtering system in order to provide overall proper system performance. For typical applications of the present microsystems, an (In, Ga)N LED is advantageous. When used in conjunction with dyes commonly employed in bioassays, a thin-film (In, Ga)N LED is advantageous.

The light source 5 typically resides on a bonding pad and reflector 4 and contains LED contact pads 6. One purpose of reflector 4 is to redirect radiation from light source 5 to sample chamber 9. Sample chamber 9 is typically a microfluidic device contained in a holder 8 for sample containment, segregation and ease of removal and replacement.

It is advantageous in some embodiments of the present invention that the sample chamber is transparent to the fluorescence-exciting radiation, thereby reducing the intensity of non-fluorescence emissions reaching the detector. For the material of the sample chamber, as well as for other components of the microsystem, it is particularly desirable that such materials do not autofluoresce when illuminated by the fluorescence-exciting radiation as such autofluorescence would, in most cases, add unacceptable levels of noise to the desired fluorescence signal produced by the sample.

The use of reflector 4 is advantageous in directing increased fluorescence-exciting radiation to the sample, but not a necessary component of a microanalytical system. Omitting the reflector may permit radiation leaving the bottom face of light source 5 to directly illuminate detector 2, thereby placing increased requirements on the filter 3. This can be avoided by using a non-reflective absorber in place of reflector 4, or using a light source that only emits in the direction of the sample, all within the scope of the present invention.

FIG. 1A depicts the generation of radiation 11 by light source 5, its transmission to the sample molecules 10 in sample chamber 9, and the re-emission of radiation 12 at a different wavelength (Stokes' shift). The re-emitted radiation passes through filter 3 for detection by photodetector 2.

Detection is typically carried out by means of avalanche photodiodes (APDs) or PIN photodiodes. While other detectors could be used, APDs and PIN photodiodes are the most commonly employed. PIN photodiodes offer the advantage of operating at lower voltages (typically less than approximately 1 volt) in comparison with APDs (typically operating from about 40 volts to about 100 volts). However, since photodiodes are not wavelength-discriminating, it is important when using such devices to separate the fluorescence emission photons selectively from the much more intense excitation light.

The region 13 can be left air-filled or filled with a substance, or combination of substances, substantially transparent to the excitation and emission radiation, for example silicon dioxide or silicon nitride. However, the substance(s) used should not have significant autofluorescence in the wavelength range used by the excitation source or by the sample emission. Autofluorescence can be a contributor to background radiation in the wavelengths ranges of emission and excitation and is disfavored in components of the system.

A support member 7 is typically used to retain and support the sample container 9. Support 7 should be transparent to the excitation and emission radiation and/or contain holes or regions of transparency sufficient for adequate radiation passage. Silicon dioxide is found to be a suitable material for some embodiments of the present invention.

A filter 3 is advantageously employed in some embodiments of the present invention but is not required in all circumstances. For those cases in which a filter is employed, it is found that thin-film filters such as those made from II-VI compounds are particularly suited, for example CdS, ZnSe among others. Filtering with CdS (and other II-VI compounds) can be adjusted to operate at other wavelengths by adding additional component(s) to the filter material to alter the bandgap.

Cadmium sulfide (CdS) has a room temperature absorption edge at about 513 nm which makes it a viable candidate for an optical filter in bioanalytical detection in which the excitation radiation of the dye is in the blue region of the spectrum (approximately 470–490 nm) and the emission is in the green (approximately 510–530 nm). As a direct bandgap semiconductor, CdS possesses a steep absorption edge resulting in a sharp transition between absorbed and transmitted wavelengths. This sharp cutoff can be important because the Stokes' shift for some dyes (e.g., YOYO—a dimeric cyanine dye) can be as small as 18 nm (Table I).

Selenium (Se) is advantageously employed to alter the bandgap of CdS. CdS and CdSe form a continuous range of solid solutions via substitution with little bandgap bowing. See, for example, Wei et al, *J. Appl. Phys.*, Vol. 87(3), pp. 1304–1311 (2000), the entire contents of which is incorporated herein by reference for all purposes. Thus, thin film filters with composition $CdS_xSe_{1-x}$ (0<x<1) can be fabricated having cutoff wavelengths varying from approximately 513 nm to approximately 714 nm (the absorption edges of CdS and CdSe respectively) by varying x from 0 to 1. See FIG. 12. Such filters would be appropriate to use in conjunction with many of the common tagging dyes, and have been shown to have relatively steep absorption edges across the composition range. See, for example, Kwok et al, *Appl. Phys. Lett.*, Vol. 52(21), pp. 1815–1816 (1988) the entire contents of which is incorporated herein by reference for all purposes.

The bandgap filters CdS, CdSe and ternary compounds of the form $CdS_xSe_{1-x}$ (0<x<1) (collectively denoted as Cd (S, Se)) will be our chief focus. However, bandgap filters consisting of (In, Ga) N offer some attractive properties including: (a) GaN has a steep absorption edge. (b) The bandgap can be tailored with the addition of varying amounts of InN. (c) The (In, Ga) N filter can, in principle, be deposited onto the same substrate as a blue (In, Ga) N LED light source.

However, the Cd (S, Se) filter system has at least two advantages over the (In, Ga) N system: (i) The absorption edge of CdS is 513 nm which is appropriately positioned for transmitting green, convenient for fluorescence detection of some important dyes. Neither InN nor GaN have an absorption edge in the visible portion of the spectrum. (ii) The Cd (S, Se) system is completely miscible due to the relatively small lattice mismatch compared to the (In, Ga) N system. Thus, our chief focus herein will be on the Cd (S, Se) system, recognizing that other bandgap filters can be constructed from different materials with different properties.

The filters described herein, chiefly CdS, $CdS_xSe_{1-x}$ (0<x<1) offer several advantages in comparison with other typical filters, such as distributed Bragg reflectors (DBRs). For example, DBRs typically display an undesirable angular dependence in their filtering properties. Angular dependence is undesirable in that fluorescence emissions from different portions of the sample strike the filter at different angles and advantageously should encounter the same filtering properties. This effect of angular nonuniformity is exacerbated when signal is collected from a wide range of incident angles, as is usually the case in practical microanalytical environments.

Figure 2A:
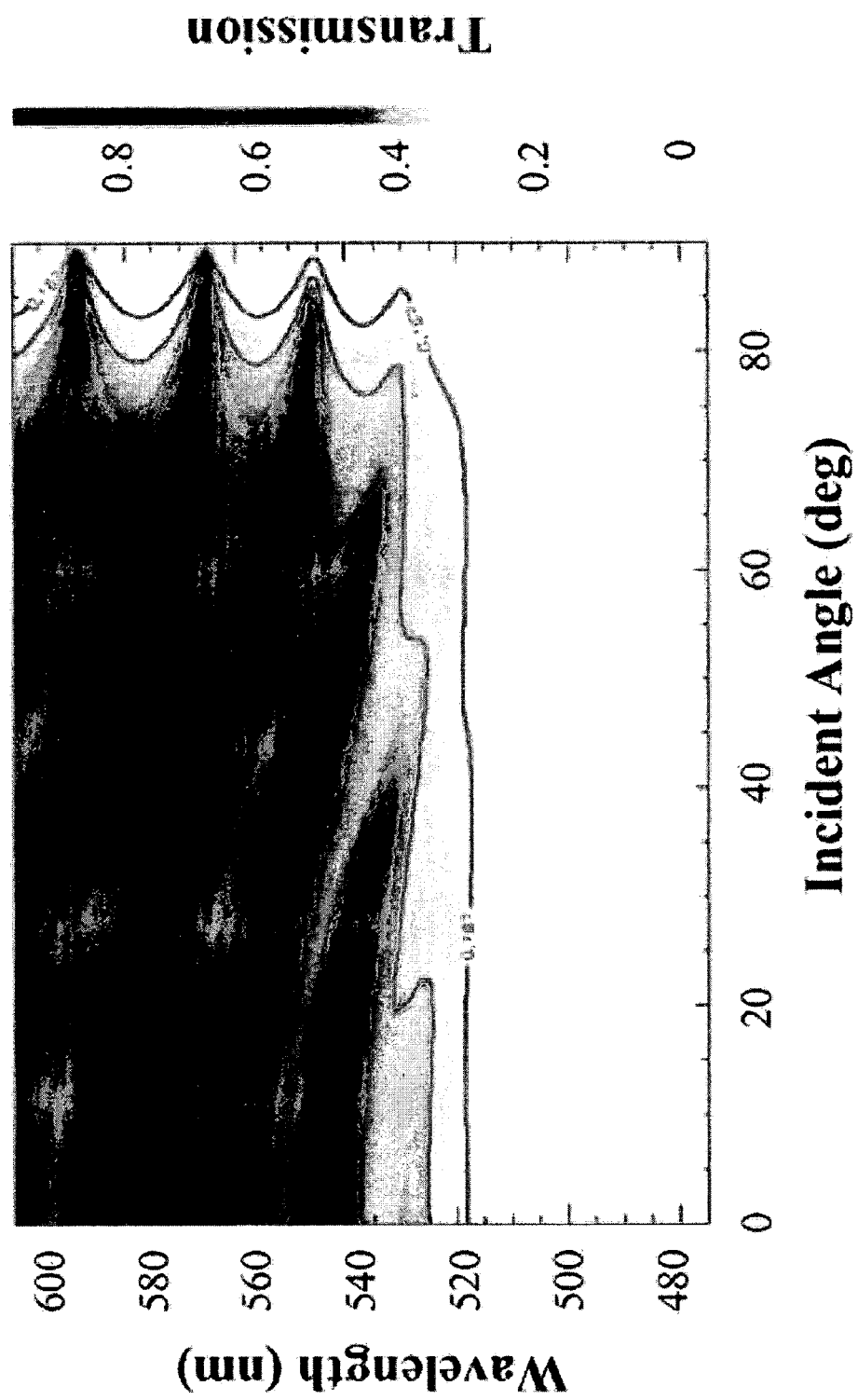
Figure 2B:
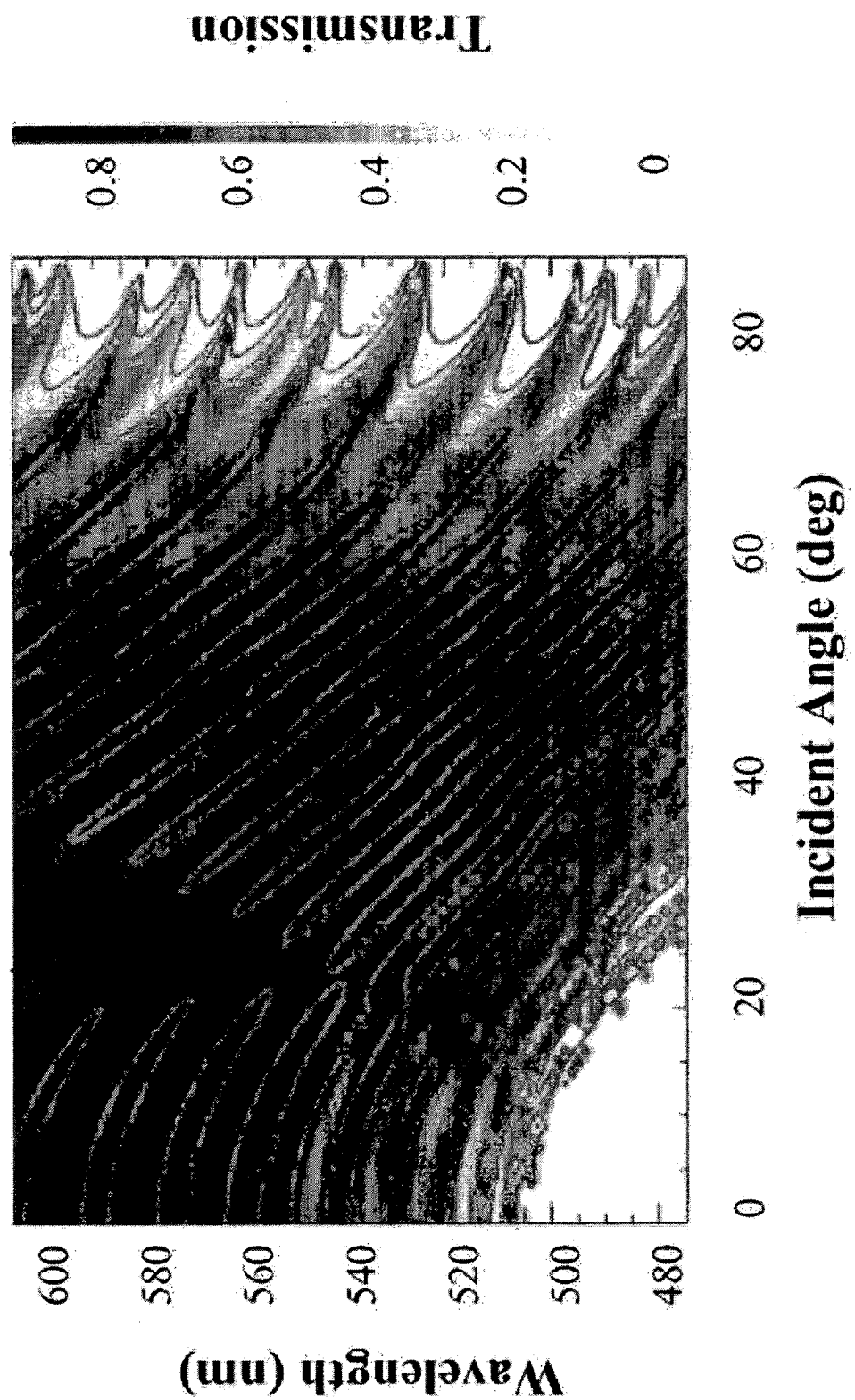
Figure 2C:
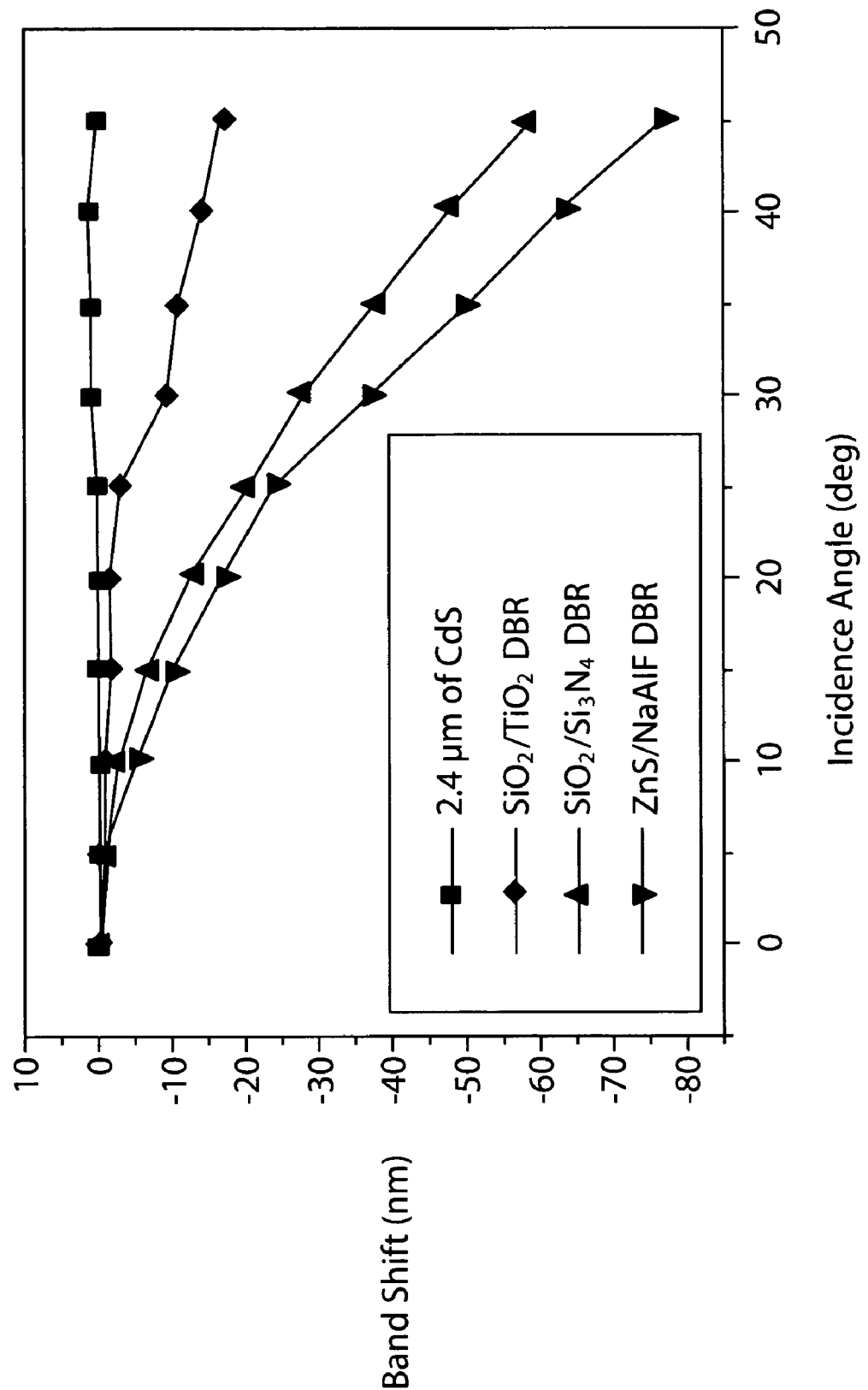

To evaluate improvements in the angular dependence of the performance of the present filters compared to DBRs, computer simulations were carried out using the IMD software from Columbia University (http://cletus.phys.columbia.edu/~windt/idl/imd/). FIG. 2A and 2B display the results of these simulations comparing the angular dependence of the CdS filter in FIG. 2A and a 90 layer ZnS/NaAlF DBR filter (Omega Optical) in FIG. 2B. The CdS filter was simulated to be 2.4 μm in thickness (μm=micrometer=micron=$10^{-6}$ meter). The improved angular uniformity of the CdS filter is clearly evident in FIGS. 2A and 2B.

The band shift as a function of incident angle is depicted in FIG. 2C, once again clearly showing the increased uniformity of the CdS filter as a function of incident angle. Comparisons are presented for an $SiO_2/TiO_2$ DBR, an $SiO_2/Si_3N_4$ DBR as well as the ZnS/NaAlF DBR.

Figure 2D:
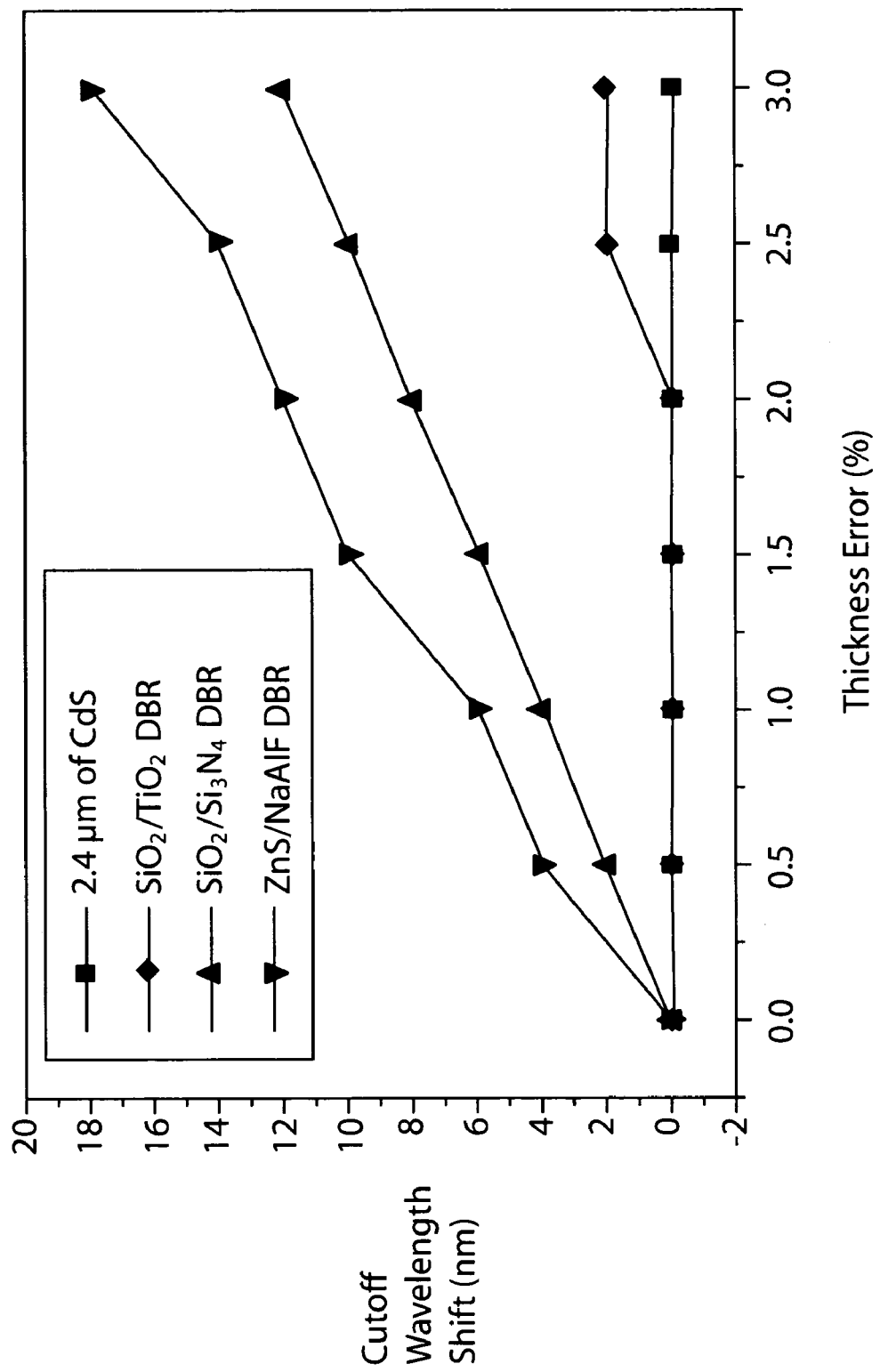

Another difficulty inherent with typical DBRs is the expensive, time-consuming and complicated DBR fabrication process, requiring precise control of deposition conditions in order to maintain the desired film thickness throughout many layers of fabrication. FIG. 2D depicts the results of simulated performance of the CdS filter in comparison with three different DBRs in which up to about 3% thickness deviation was simulated. As is clear from FIG. 2D, the CdS filter is markedly less sensitive to thickness variations and, therefore, not as demanding of precise process controls.

For the fabrication of both CdS and $CdS_xSe_{1-x}$ filters, pulsed laser deposition (PLD) typically allows good compositional control and, therefore, is a favorable deposition technique for prototype fabrication or fabrication of limited numbers of filters. For large scale integration (i.e., batch fabrication) thermal evaporation from two sources can be employed, especially for compounds that sublime congruently. Sputtering is another candidate deposition technique. Different filter compositions can be deposited on different regions of the substrate using sequential masking.

The LED structure is conveniently transferred from the sapphire substrate, upon which such devices are typically grown, to the photodetector by a two-step, "pixel-to-point" laser lift-off process. Aspects of this process have been described by Z. S. Luo et al, "Enhancement of (In, Ga)N Light-Emitting Diode Performance by Laser Liftoff and Transfer from Sapphire to Silicon," *IEEE Photonics Technology Letters*, Vol. 14, pp. 1400–1402 (October 2002), the entire contents of which is incorporated herein by reference for all purposes. Other aspects are described in Attachment C hereto, Z. S. Luo et al, "Pixel-to-Point Transfer: A Process for Integrating Individual GaN-Based Light-Emitting Devices into Heterogeneous Microsystems" *Mat. Res. Soc. Symp. Proc.*, Vol. 768, pp. G4.8.1–G4.8.5 (2003), the entire contents of which is made a part hereof and incorporated herein by reference for all purposes. Briefly described, the separation mechanism of laser lift-off has the laser beam passing through the substrate (such as sapphire) to which the LED is attached. Upon striking the interface where the first layer of the LED starts (e.g., the gallium nitride layer), the material of this layer is decomposed, which substantially weakens the bonding between the LED and the substrate. Mechanical separation of the LED from its substrate is then feasible, perhaps assisted by heating to soften and/or melt the decomposition product(s) (for example, the melting point of the metallic Ga decomposition product is modest, about 29 deg. C.).

In typical embodiments, the pixel-to-point transfer process involves three steps as depicted schematically in FIG. 3 for a LED conveniently grown on a sapphire substrate. Epitaxial growth constraints on the fabrication of typical LEDs make the use of sapphire substrates an advantageous growth platform. In the first step, the LED on its sapphire substrate is attached to a pick-up rod by a suitable adhesive. The commercial adhesive known as SUPER-GLUE is found to give adequate performance although other adhesives are not excluded. The second step involves passing a laser beam through the sapphire substrate, resulting in laser lift-off of the LED from the substrate. An excimer laser is advantageously employed to effect the laser lift-off step, typically in conjunction with Pd—In transient liquid-phase bonding. Transient liquid-phase bonding or diffusion soldering is advantageously used to form strong and high-temperature stable bonds at moderate bonding temperatures and short bonding times in comparison with other techniques such as solid-state diffusion bonding. The third step involves the formation of a bond between the LED and the designated region of the microsystem (silicon or other substrate), followed by the removal of the pick-up rod. This laser lift-off and transfer technique has been applied to an (In,Ga)N LED without significant degradation in LED performance. FIG. 4 depicts the electroluminescence spectra (emission spectra) of the LED before (a) and after (b) the lift-off and transfer from sapphire to silicon. The intensity of FIG. 4 is given in arbitrary units.

In addition to the processes described and referenced elsewhere herein, "pixel-to-point" includes a more general step-and-repeat process as well as transfer processes omitting the pick-up or transfer rod (typically glass), and/or omitting dicing the sapphire substrate. See, for example, U.S. Pat. Nos. 6,420,242; 6,335,263; 6,071,795, the entire contents of which are incorporated herein by reference for all purposes.

In addition, various modifications and variations are included in "pixel-to-point." For example, another embodiment includes an automated stepper for placing the pick-up rod on a device mesa defined by etching on the sapphire substrate. The pick-up rod typically includes a layer of adhesive (e.g., polymer, metal, alloy, among others). With pressure applied, the bond could be made, possibly with the local application of radiation and/or heat. For example, if the adhesive is a radiation-curable adhesive (typically UV curable), the UV could be directed down the rod. In other examples, if the adhesive is a metal or alloy with a relatively low melting point, a laser pulse directed down the rod could melt the metal to achieve the bond. A pulse of laser or other radiation could be used to heat a thermally-curable adhesive and thereby achieve the desired bond. Once bonded, the GaN (or other device) can be transferred by means of laser irradiation incident on the GaN-sapphire interface from the opposite side of the sapphire to initiate device lift-off. Once transferred, the rod can be moved to the substrate on which the microsystem is under construction where a more permanent bond can be made (such as Pd—In, among others), and the bond to the transfer rod can be released (for example, by heating an In or other thermally-releasable bond above its melting point—157 deg. C. for In—or by using a UV or other laser pulse to delaminate a polymer bond, among other methods). Other variations of the pixel-to-point transfer process are apparent to those having ordinary skills in the art and are included within its scope.

The structures and techniques described herein are not limited to a single source of radiation probing a single sample chamber. FIG. 5 depicts two light sources 5a and 5b (typically including reflectors 4a, 4b) positioned to direct exciting radiation onto a single sample container 9, with emitted radiation passing through filters 3a and 3b to detectors 2a and 2b. While FIG. 5 depicts two light sources, more than two can be employed as determined by geometric and fabrication considerations, among other factors. The microanalytical system depicted in FIG. 5 would be capable of probing a sample at two different wavelengths concurrently, thereby probing the sample for approximately twice as much data as the system of FIG. 1.

A typical example of a two-color fluorescence detection microsystem pursuant to some embodiments of the present invention is depicted in schematic cross-sectional view in FIG. 13. Each filter, filter 1 or filter 2 respectively in FIG. 13, can advantageously be tailored to "match" its associated LED such that the filter effectively blocks the excitation energy emitted by the electroluminescence of its associated LED, LED 1 or LED 2. Thus, only the dye emission is transmitted by the filter indicating that the dye is also chosen to match the LED-filter combination.

Cross-contamination of light emitted by LED 1 (or its associated dye) reaching filter 2, or visa versa, in any significant intensity is unlikely due to the geometry and spacing of the components in FIG. 13. However, in those cases in which such cross-contamination is a concern, the filters are advantageously tailored, and/or the detectors are appropriately positioned geometrically, to take this into account as well and to reduce its effect to acceptable levels. The problem can also be mitigated by time modulation of the excitation sources and/or detectors. That is, LED 2 can be off when LED 1 is on and vice versa. The modulation frequency can be engineered to be limited only by the fluorescence lifetime.

The possibility of probing a sample at multiple wavelengths simultaneously as depicted in FIG. 5 and FIG. 13 is facilitated by the laser lift-off and transfer techniques that allow individual LEDs to be lifted off a source wafer and placed at specific locations on the microsystem substrate above the photodetector(s). That is, multicolor LEDs can be positioned as desired on the same substrate. Thus, the LEDs need not be fabricated on and transferred from the same substrate, thereby enabling integration of multiple LEDs (such as (In,Ga)N) with electroluminescence peaks ranging from the UV through the green portion of the visible spectrum, and beyond as LED or other light sources become available. Likewise, filters deposited onto individual photodetectors need not be of the same composition and could filter at different wavelengths. This type of flexibility can also be brought to larger systems, such as wafer scale devices making use of large-area lift-off and transfer techniques.

It is feasible with the present microanalytical system to monitor the state of a reaction as a function of time by tracking the time-dependence of the fluorescence signal. That is, in-situ evaluations of chemical reactions as a function of time are realizable whenever the fluorescence signal of the reacting chemicals is a function of the reaction state (i.e., the extent to which the reaction has proceeded) for reactions in which the progress of the reactions alters the fluorescence. For example, a mixture of reactants introduced into the sample chamber permits the progress of a fluorescence-altering reaction (or other process) to be monitored. One or more reactants and/or catalysts can be placed into the sample chamber while one or more reactants and/or catalysts can be introduced from outside the sample chamber, by injection through a port or by other means, and the time-dependence of the resulting process tracked.

However, the use of multiple or multicolored LEDs (or other light sources) allow one light source to initiate a photochemical reaction, whose progress can then be monitored by other LEDs. While such reaction-promoting radiation can be imposed on the sample chamber from outside, it is convenient in some embodiments of the present invention to make use of the multiple-LED structure to facilitate photochemical initiation. Appropriate triggering and timing circuits can be used to follow the progress of such fluorescence-altering processes within the sample chamber.

As an illustrative example of a microsystem pursuant to some embodiments of the present invention, we describe the heterogeneous integration into a microanalytical system of a CdS filter, an (In, Ga)N blue LED, a Si PIN photodetector and disposable poly(dimethylsiloxane) (PDMS) microfluidic channels. A schematic, cross-sectional depiction is given in FIG. 6(a) and a typical wiring arrangement to both the LED and the photodetector is depicted in FIG. 6(b). Typically, biases of about 15 V (volts) for the photodetector and about 4.5 V for the LED are advantageously applied.

FIG. 7 depicts in schematic cross-sectional view, the path of the exciting light from the LED to the sample, and the return path of the emitted light to the p-i-n (or PIN) photodetector.

Rather than employing microlenses to couple the excitation light beams into the sample chamber and the microchemical components, the fluorescence detection microsystem pursuant to some embodiments of the present invention is considerably simpler, typically using direct, normal or near-normal incidence of the excitation light from an integrated light source in close proximity to the sample. Typically, the light source is located about 2 mm from the sample.

In typical laser-induced fluorescence (LIF) analytical systems, a significant source of noise relates to emissions from the source of excitation radiation that occur in the emission wavelength range of the dye. That is, spectral components from the light source typically have some finite width that can spill over into the wavelength region of the Stokes' shifted emission radiation. Table I illustrates that Stokes' shifts can be rather small so even rather sharp excitation radiation sources can still lead to noise. However, the present configuration of components in the microsystem places the detector and the light source on the same side of the sample, thus requiring backscattering of the noise component of radiation to reach the detector. This configuration substantially reduces such noise in comparison with other LIF systems having the detector on the opposite side of the sample from the light source.

A reflective material, typically aluminum, (denoted as 4 in FIG. 1) placed beneath the LED substantially eliminates backside emissions from the LED and significantly enhances the frontside excitation signal. In this configuration, the light from the LED not absorbed by the sample in chamber 9 passes through the microfluidic components 8 and does not reach detector 2 with any significant intensity. The emitted fluorescent signal from the sample is incident on the detector from a direction opposite (anti-parallel) to the primary emission cone from the LED excitation source. In contrast, placing the detector behind the microfluidic components 8 (in the direct path of the light from the LED), would result in all spectral components emitted by the LED (including those in the emission range of the dye) being directly incident on the detector. The anti-parallel configuration significantly reduces the background noise reaching the detector.

In fact, the anti-parallel configuration may sufficiently reduce background noise such that the filter 3 becomes superfluous and can be omitted. This is advantageous in reducing fabrication complexity and costs but also can increase detection sensitivity for the microsystem. Typical optical filters are not 100% transmissive of the light emitted by the sample. For example, a CdS filter 2.4 µm thick transmits about 40% of the green emitted light following excitation of the dye by a blue LED. Without this 60% loss of intensity to the filter, the increased intensity of emitted light reaching the photodetector would increase the sensitivity of the instrument (that is, decrease the emitted signal required for detection which means decreasing the amount of sample required for detection). Even if the filter cannot be entirely dispensed with, the sensitivity of the microsystem can also be increased by the use of one or more anti-reflective coatings on the filter, within the scope of the present invention.

In addition to reducing background noise, the anti-parallel configuration of components facilitates the replacement of disposable microfluidic components and samples. That is, since the light source, photodetector and filter (if any) are located on a single monolithic substrate, the sample chamber and associated microfluidics can be readily removed and replaced without disturbing these optical components.

Fluorescence signal exiting from the backside (upward) portion of a transparent microfluidic component 8, such as PDMS, is not collected by the photodetector. A reflective surface or mirror can be added to the upper surface of 8 causing fluorescence signal to be reflected back towards the photodetector thereby increasing the amount of emitted signal that is detected. However, unless a wavelength-sensitive reflector is employed, the direct LED excitation signal would also be reflected to the detector, potentially contributing unacceptably to the noise. Thus, a mirror or reflector above the microfluidics would be advantageous in those cases in which the additional noise reaching the detector is manageable and its deleterious effects are judged less significant than the advantages of additional fluorescence signal reaching the detector.

A typical fabrication process for a microanalytical system pursuant to some embodiments of the present invention is as follows:

A layer approximately 1500 Å thick (Å=Angstrom=$10^{-10}$ meter) of an insulator is deposited onto a silicon photodiode substrate. Plasma-Enhanced-Chemical Vapor-Deposition (PECVD) is a useful deposition technique and silicon dioxide $SiO_2$ is a typical insulator.

A layer of indium-tin-oxide (ITO) having a thickness from approximately 200 Å to approximately 2000 Å is deposited onto the insulating layer. Sputter deposition is advantageously employed at approximately 300 W (watts) of power in an RF magnetron sputtering system with gas flow rates of approximately 95 sccm (standard cubic centimeters per minute) Ar and 5 sccm of $Ar/O_2$, that is, approximately 20% concentration of $O_2$ in Ar. The gas pressure is approximately 4 milliTorr. Under these conditions, the deposition rate is approximately 200 Å/min.

A film of CdS, having a thickness from approximately 1 µm to approximately 3 µm (1 µm=$10^4$ Å), is deposited onto the $ITO/SiO_2$ stack. Pulsed laser deposition (PLD) is advantageously employed. A typical PLD system employing a KrF excimer laser is depicted schematically in FIG. 8. Under such conditions, the $SiO_2$ layer provides electrical insulation and also serves as a diffusion barrier, substantially reducing or preventing diffusion of the deposited species into the active area of the photodiode during PLD. Since ITO is conductive, electrical insulation is needed to avoiding shorting the n-contacts of the LED. The $SiO_2$ layer also provides insulation between the ITO and the p- and n- contacts of the LED.

The PLD technique typically employs a solid target (for example, approximately 1.3 cm in diameter and approximately 0.65 cm thick), as typically used in evaporation or sputtering. A laser pulse of approximately 38 ns (nanosecond) duration and fluence of approximately 3 Joules/cm$^2$ is applied to the target at a pulse frequency of approximately 10 Hz. A base pressure of approximately $(4-7)\times10^{-5}$ Pascals, substrate temperature of approximately 350 deg. C., and target-to-substrate distance of approximately 6.2 cm were used. Under these conditions, the deposition rate is approximately 0.5 Å per pulse. A film approximately 2.4 μm in thickness exhibited approximately 500 Å of surface roughness. Faster deposition rates can be obtained by placing the substrate closer to the target but at the expense of greater non-uniformity in thickness.

The (In,Ga) N LED, (commonly grown on sapphire due to the constraints of epitaxial growth), is transferred onto the pre-fabricated silicon photodiode substrate by a pixel-to-point double transfer technique using an excimer laser lift-off and Pd—In transient liquid phase bonding. The pixel-to-point process typically involves three steps: i) temporarily bonding the LED pixel to a specially designed pick-up rod with sapphire substrates facing up using, for example, Super Glue®. ii) Removing the sapphire substrates using laser lift-off. iii) Permanently bonding the LED pixel to a designated area.

Metallization (for example, with aluminum) to form contacts for the LED and the photodiode completes the fabrication of the non-disposable substrate for the microanalytical system. Wirebonding could also be used.

A disposable microchannel filled with a fluid containing a fluorescent dye (or other molecule to be probed), is positioned on top of the substrate. It is envisioned that the typical microanalytical device will have a disposable microchannel sample container removably positioned atop a reusable substrate. This configuration typically facilitates sequential field use of the electronic and optical components on the substrate, but is not an inherent limitation of the present invention. Components that are typically disposable are denoted by 7, 8 and 9 in FIG. 1.

The disposable microchannels are advantageously fabricated on a PDMS mold. These molds are advantageously prepared by means of deep-reactive ion etching (DRIE) as depicted in FIG. 9. Various mask designs can be used in connection with various embodiments of the present invention with a view towards increasing the area from which the fluorescent signal emitted from the dye can be collected. Microchannel depths typically vary from approximately 20 μm to approximately 150 μm, and channel widths of approximately 50 μm, 100 μm, 1 mm and 2 mm have been used.

The fabrication process described herein has been used to fabricate a prototype microanalytical system including a 1.2 μm CdS filter. Fluorescence detection data obtained with this prototype is given in FIG. 10 in which the emission signal at the detector is shown as a function of molar concentration (M=moles/liter). Carboxylate-modified microspheres were used, obtained from Molecular Probes, Inc. of Eugene, Oreg. The microspheres were approximately 0.04 μm in diameter in a PDMS microfluidic channel approximately 2 mm wide and 100 μm deep excited by a blue LED at maximum intensity (biased to 4.5 V and drawing approximately 20–25 milliAmp-mA). Three measurements were recorded at each concentration and the error bars depicted on FIG. 10 represent two standard deviations (2–20 microvolt) both above and below the average. The lowest detectable concentration is estimated to be about $1.2 \times 10^{-7}$ M of fluorescein microspheres. FIG. 11 shows the prototype microsystem with the LED power on (a) and exciting a sample in the microfluidic device (b).

Another approach to an integrated microanalytical system and its fabrication relates to the vertical integration of excitation, filtering and photodetection in a stack approximately 10 μm thick. This stack is integrated with a microfluidic channel structure that can be made from various materials including (but not limited to) polymeric solids such as PDMS or parylene, among others, or structural ceramics such as silicon nitride, among others.

In this approach, a microchannel is typically formed in a silicon substrate. This channel is sealed with a thin layer of material, typically polyimide several microns in thickness.

The polyimide layer or seal typically covers substantially all component-containing areas of the substrate. Thus, a region of the polyimide seal is etched away on the substrate at a region away from the microchannel so that a metallic contact can be deposited. This contact is advantageously p-doped which can be accomplished by a subsequent diffusion doping, or by subsequent implantation doping.

A LED, typically (In,Ga)N, or other light source, is bonded to the silicon substrate that has been prepared by the preceding steps. The top side of the LED stack is bonded to the substrate, and in such location that the metallic contact previously formed functions as the p-contact to drive the LED. The LED is conveniently removed from the sapphire substrate on which is it typically grown and transferred to the silicon substrate by means of a laser lift-off technique as discussed elsewhere.

A film of a II-VI compound is deposited directly onto the n-type (In,Ga)N LED, typically having a thickness in the range from approximately 2–4 μm. Typical II-VI compounds include CdS, $CdS_xSe_{1-x}$, $CdS_xTe_{1-x}$ (0<x<1), ZnSe, among others. It is advantageous that the deposited film have a steep absorption band edge, more typical of polycrystalline films rather than amorphous films. ZnSe, with an absorption edge at approximately 470 nm is a favorable candidate.

An insulating layer is advantageously deposited as a buffer. $SiO_2$ is typically employed although other materials (such as $Si_3N_4$, among others) could also be used.

A transparent conductor is deposited onto the insulting buffer layer to serve as a ground contact for both the LED and the photodetector. Indium-tin-oxide (ITO) is typically used.

N-type CdS is deposited onto the ITO followed by the deposition of p-type CdTe. The CdS/CdTe form a p-n photodetector.

The use of II-VI p-n junction photodetectors (e.g., CdS/CdTe) offers several advantages over the use of crystalline silicon. Silicon is an indirect bandgap semiconductor whereas both CdS and CdTe are direct bandgap semiconductors. That is, an electron making a transition between bands can do so in direct bandgap semiconductors without changing its momentum, which leads to a sharp absorption edge occurring at the bandgap energy (corresponding to a particular wavelength λ=(Planck's constant)/energy). Sharp absorption edges, as in direct bandgap semiconductors, are advantageous in wavelength-sensitive detection devices.

In contrast, electron transitions from valence band to conduction band in an indirect bandgap semiconductor require a change in the electron's momentum, which occurs through the electron's coupling with the vibrational modes of the surrounding lattice (phonons) in order to conserve total momentum. Thus, indirect bandgap materials, such as silicon, tend to have low absorption coefficients, which means that a relatively large volume of material is needed for efficient absorption and detection of incident radiation. In other words, Si has a relatively low quantum efficiency due to its bandgap structure. Therefore, a thinner photodetector can be used if one employs a direct bandgap material such as a II-VI material, as in some embodiments of the present invention.

In addition to having sharp absorption edges, II-VI compounds typically offer other advantages as well. For example, dark current densities in CdS/CdTe solar cells have been reported as varying between approximately $3.5 \times 10^{-4}$ A/mm$^2$ at 313 deg. K to approximately $1.9 \times 10^{-8}$ A/mm$^2$ at 224 deg. K. McCandless et al, *Prog. Photovolt. Res. Appl.*, Vol. 7, pp. 21–30 (1999). In contrast, since Si has a relatively small bandgap (approximately 1.1 eV-electron volt), the dark currents occurring in Si are typically significantly larger than in II-VI semiconductors. In fact, Si photodetectors typically need to be cooled in order to achieve high sensitivity.

II-VI semiconductors typically can be tuned so as to have bandgaps falling within the visible range of the electromagnetic spectrum (approximately 2–3 eV). For example, the bandgap in CdS is approximately 2.45 eV and approximately 2.7 eV in ZnSe.

A possible photodetector such as ZnSe has been reported as having a dark current density of approximately $10^{-8}$ A/cm$^2$, an ideality factor of approximately 1.1 and a barrier height of approximately 1.17 eV. The responsivity of ZnSe above the bandgap has been measured to be approximately 0.1 A/W and its bandgap exhibits a sharp cutoff of 3–4 orders of magnitude at approximately 460 nm. ZnSe photodiodes fabricated on GaAs have a quantum efficiency of approximately 62% in blue light. See McCandless et al, supra.

For ZnMgSSe structures, Faschinger et al, (*J. Cryst. Growth*, Vol. 214(5), (2000), pp. 1138–1141, the entire contents of which are incorporated herein by reference for all purposes) have reported dark current densities as low as about $10^{-12}$ A/mm$^2$ at reverse voltages between about 0 and 5 V, which is about one fifth of the value for high quality Si diodes. These authors assert that the use of ZnMgSSe and ZnSTe/ZnTe allow the energy gap of the detector to be tuned between approximately 2.1 eV and approximately 3.2 eV (the visible and into the UV region of the spectrum).

Although various embodiments which incorporate the teachings of the present invention have been shown and described in detail herein, those skilled in the art can readily devise many other varied embodiments that still incorporate these teachings.

What is claimed is:

1. A light source and detector comprising:
   a) a light source capable of producing exciting radiation and having a location so as to direct said exciting radiation from a first face of said light source onto a sample, wherein said sample is capable of undergoing fluorescence when illuminated by said exciting radiation and producing emitted radiation having a different wavelength from said exciting radiation;
   b) said light source having a second face located on the opposite side of said light source from said first face;
   c) a detector capable of detecting said emitted radiation and having a location so as to receive at least a portion of said emitted radiation from said sample;
   d) wherein said light source and said detector are integrally combined on a single substrate; and
   e) said detector is located generally adjacent to said second face and not directly illuminated by said exciting radiation emitted from said first face.

2. A light source and detector as in claim 1 further comprising a filter interposed between said detector and said sample so as to intercept said emitted radiation, wherein said filter transmits at least a portion of said emitted radiation to said detector and blocks said exciting radiation from reaching said detector.

3. A light source and detector as in claim 2 wherein said filter is a thin-film bandgap filter.

4. A light source and detector as in claim 2 wherein said filter is a II-VI semiconductor.

5. A light source and detector as in claim 2 wherein said filter is CdS.

6. A light source and detector as in claim 2 wherein said filter is a compound having the chemical formula $CdS_xSe_{1-x}$ wherein x is a number between zero and one.

7. A light source and detector as in claim 2 wherein said filter is (In,Ga)N.

8. A light source and detector as in claim 1 further comprising a reflector adjacent to said second face of said light source opposite said first face wherein said reflector reflects radiation emitted from said second face of said light source in generally the same direction as said exciting radiation emitted from said first face.

9. A light source and detector as in claim 1 wherein said light source is a light emitting diode.

10. A light source and detector as in claim 9 wherein said light emitting diode is (In,Ga)N.

11. A light source and detector as in claim 1 further comprising a non-reflecting absorber interposed between said detector and said sample so as to intercept said emitted radiation, wherein said non-reflecting absorber transmits at least a portion of said emitted radiation to said detector and blocks said exciting radiation from reaching said detector.

12. A light source and detector as in claim 1 further comprising a reflector located on the side of said sample opposite of said light source and said detector, wherein said reflector reflects fluorescence emitted from said sample in a direction away from said detector in a new direction toward said detector.

13. A light source and detector for an integrated multiwavelength microanalytical system comprising:
   a) at least two light sources, said light sources having a first face for emitting exciting radiation and having a second face located on the opposite side of said light source from said first face, wherein each of said light source is capable of producing said exciting radiation at a different wavelength, and wherein each of said wavelengths is capable of producing fluorescence emissions when directed onto a sample;
   b) a separate detector associated with each of said light sources located generally adjacent to said second face and not directly illuminated by said exciting radiation emitted from said first face, wherein each of said detectors is capable of detecting the fluorescence emissions produced by illuminating said sample with each of said light sources associated with each of said detectors, and
   c) wherein said light sources and said detectors are integrally combined on a single substrate.

14. A light source and detector as in claim 13 further comprising filters interposed between each of said detectors and said sample so as to intercept said fluorescence emissions from said sample, wherein said filters transmit at least a portion of said fluorescence emission produced by said illumination of said sample by said light source associated with each of said detectors and blocks said exciting radiation produced by said light source associated with each of said detectors.

15. A microanalytical system comprising:
   a) a light source producing fluorescence-exciting radiation said light source having a first face for emitting said fluorescence-exciting radiation and having a second face located on the opposite side of said light source from said first face, and a detector, said detector located generally adjacent to said second face and not directly illuminated by said fluorescence-exciting radiation emitted from said first face, capable of detecting fluorescence emissions from a sample, wherein said light source and said detector are integrally combined on a single substrate;

b) a chamber containing a sample wherein said chamber is located so as to intercept at least a portion of said fluorescence-exciting radiation from said light source and to direct at least a portion of the fluorescence emissions from said sample to said detector.

16. A microanalytical system as in claim 15 further comprising a filter interposed between said detector and said sample so as to intercept said fluorescence emissions from said sample, wherein said filter transmits at least a portion of said fluorescence emissions to said detector and blocks said fluorescence-exciting radiation from reaching said detector.

17. A microanalytical system as in claim 15 wherein said chamber and said sample therein is capable of separation from said light source and said detector, and replacement.

18. A microanalytical system as in claim 15 wherein the material of said chamber is substantially transparent to said fluorescence-exciting radiation.

19. A microanalytical system as in claim 15 wherein the material of said chamber is a polymeric solid or a structural ceramic.

20. A microanalytical system as in claim 19 wherein the material of said chamber is poly (dimethylsiloxane) or parylene.

* * * * *